(12) United States Patent
Willis et al.

(10) Patent No.: US 8,003,733 B2
(45) Date of Patent: Aug. 23, 2011

(54) PROCESS FOR PREPARING SULFONATED BLOCK COPOLYMERS AND VARIOUS USES FOR SUCH BLOCK COPOLYMERS

(75) Inventors: Carl Lesley Willis, Houston, TX (US); Dale Lee Handlin, Jr., Houston, TX (US); Scott Russell Trenor, Houston, TX (US); Brian Douglas Mather, Blacksburg, VA (US)

(73) Assignee: Kraton Polymers US LLC, Houston, TX (US)

( * ) Notice: Subject to any disclaimer, the term of this patent is extended or adjusted under 35 U.S.C. 154(b) by 0 days.

(21) Appl. No.: 12/764,010

(22) Filed: Apr. 20, 2010

(65) Prior Publication Data

US 2010/0203784 A1    Aug. 12, 2010

Related U.S. Application Data

(62) Division of application No. 11/458,856, filed on Jul. 20, 2006, now Pat. No. 7,737,224.

(60) Provisional application No. 60/701,768, filed on Jul. 22, 2005.

(51) Int. Cl.
*C08F 8/34* (2006.01)

(52) U.S. Cl. ............... 525/333.5; 525/313; 525/314; 525/315; 525/316; 525/291; 525/330.3; 525/330.4; 526/287; 526/319; 526/328; 526/328.5; 526/329; 526/329.2; 526/329.7

(58) Field of Classification Search ............... 525/313, 525/314, 315, 316, 291, 333.5, 331.9, 332.8, 525/332.9, 333.1, 333.2; 526/287
See application file for complete search history.

(56) References Cited

U.S. PATENT DOCUMENTS

| | | | |
|---|---|---|---|
| 3,670,054 A * | 6/1972 | De La Mare et al. ......... | 525/314 |
| 3,735,559 A | 5/1973 | Salemme | |
| 4,157,432 A * | 6/1979 | Lundberg et al. ............ | 525/344 |
| 4,678,025 A | 7/1987 | Oberlander et al. | |
| 4,728,429 A | 3/1988 | Cabasso et al. | |
| 4,766,161 A | 8/1988 | Chlanda et al. | |
| 4,909,810 A | 3/1990 | Nakao et al. | |
| 4,931,070 A | 6/1990 | Prasad | |
| 4,934,148 A | 6/1990 | Prasad et al. | |
| 4,944,776 A | 7/1990 | Keyser et al. | |
| 5,095,054 A | 3/1992 | Lay et al. | |
| 5,239,010 A * | 8/1993 | Balas et al. .................... | 525/314 |
| 5,288,773 A | 2/1994 | Gorbaty et al. | |
| 5,348,691 A | 9/1994 | McElroy et al. | |
| 5,468,574 A | 11/1995 | Ehrenberg et al. | |
| 5,516,831 A * | 5/1996 | Pottick et al. ................. | 524/474 |
| 5,620,500 A | 4/1997 | Fukui et al. | |
| 5,677,074 A | 10/1997 | Serpico et al. | |
| 5,679,482 A | 10/1997 | Ehrenberg et al. | |
| 5,679,745 A | 10/1997 | Hamada et al. | |
| 5,785,117 A | 7/1998 | Grinbergs | |
| 5,840,387 A | 11/1998 | Berlowitz-Tarrant et al. | |
| 6,033,804 A | 3/2000 | Doyle et al. | |
| 6,110,616 A | 8/2000 | Sheikhali et al. | |
| 6,145,588 A | 11/2000 | Martin et al. | |
| 6,306,419 B1 | 10/2001 | Vachon et al. | |
| 6,383,391 B1 | 5/2002 | Ehrenberg et al. | |
| 6,413,298 B1 | 7/2002 | Wnek et al. | |
| 6,536,514 B1 | 3/2003 | Sugiyama et al. | |
| 6,579,948 B1 | 6/2003 | Tan et al. | |
| 6,664,309 B2 | 12/2003 | Svenningsen et al. | |
| 6,664,340 B1 | 12/2003 | Karki et al. | |
| 6,703,446 B2 | 3/2004 | Schwindeman et al. | |
| 6,777,082 B2 | 8/2004 | Patel et al. | |
| 6,838,391 B2 | 1/2005 | Harle | |
| 6,841,601 B2 | 1/2005 | Serpico et al. | |
| 7,029,559 B2 | 4/2006 | Won et al. | |
| 7,152,670 B2 | 12/2006 | Dobbs et al. | |
| 7,160,551 B2 | 1/2007 | McHughy et al. | |
| 7,179,860 B2 | 2/2007 | Cao et al. | |
| 7,188,666 B2 | 3/2007 | Lee et al. | |
| 7,228,891 B2 | 6/2007 | Shin et al. | |
| 7,231,967 B2 | 6/2007 | Haglid | |
| 7,307,127 B1 | 12/2007 | Napadensky et al. | |
| 7,309,522 B2 | 12/2007 | Webb et al. | |
| 7,320,361 B2 | 1/2008 | Arai et al. | |
| 7,598,337 B2 | 10/2009 | Hung et al. | |
| 7,601,785 B2 | 10/2009 | Chang et al. | |
| 7,754,844 B2 | 7/2010 | Sakaguchi et al. | |
| 7,807,759 B2 | 10/2010 | Shin et al. | |
| 7,851,575 B2 | 12/2010 | Ravikiran et al. | |
| 2001/0053475 A1 | 12/2001 | Ying et al. | |
| 2003/0106680 A1 | 6/2003 | Serpico et al. | |
| 2003/0219671 A1 * | 11/2003 | Tanma et al. ............... | 430/110.4 |
| 2003/0228681 A1 | 12/2003 | Ritts et al. | |
| 2004/0005490 A1 | 1/2004 | Fan et al. | |
| 2004/0101753 A1 | 5/2004 | Hwang et al. | |
| 2004/0137813 A1 | 7/2004 | Faucher | |
| 2004/0142910 A1 | 7/2004 | Vachon et al. | |
| 2005/0133204 A1 | 6/2005 | Gates et al. | |
| 2005/0137349 A1 * | 6/2005 | Bening et al. ................. | 525/314 |

(Continued)

*Primary Examiner* — Vasu Jagannathan
*Assistant Examiner* — Robert C Boyle
(74) *Attorney, Agent, or Firm* — Novak, Druce & Quigg LLP; Michael A. Masse

(57) ABSTRACT

A process for preparing sulfonated block copolymers that are solid in water having at least two polymer end blocks A and at least one polymer interior block B involving sulfonating the interior block B until substantially sulfonated. Each A block having one or more segments selected from polymerized (i) para-substituted styrene monomers, (ii) ethylene, (iii) alpha olefins of 3 to 18 carbon atoms; (iv) hydrogenated 1,3-cyclodiene monomers, (v) hydrogenated monomers of conjugated dienes having a vinyl content less than 35 mol percent prior to hydrogenation, (vi) acrylic esters, (vii) methacrylic esters, and (viii) mixtures thereof. Each B block having segments of one or more polymerized vinyl aromatic monomers selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof.

18 Claims, 3 Drawing Sheets

U.S. PATENT DOCUMENTS

| | | |
|---|---|---|
| 2005/0266290 A1 | 12/2005 | Sun et al. |
| 2006/0154126 A1 | 7/2006 | Ritts et al. |
| 2008/0085437 A1 | 4/2008 | Dean et al. |
| 2008/0305251 A1 | 12/2008 | Fukuta et al. |
| 2009/0126370 A1 | 5/2009 | Tsai |
| 2009/0246593 A1 | 10/2009 | Nowatari et al. |
| 2009/0263699 A1 | 10/2009 | Sadasue et al. |
| 2009/0314480 A1 | 12/2009 | Grinbergs et al. |
| 2010/0031817 A1 | 2/2010 | Ehrenberg et al. |
| 2010/0159353 A1 | 6/2010 | Ohgi et al. |
| 2010/0167100 A1 | 7/2010 | Moore et al. |
| 2010/0167159 A1 | 7/2010 | Ono et al. |
| 2010/0170776 A1 | 7/2010 | Ehrenberg et al. |
| 2010/0233569 A1 | 9/2010 | Ono et al. |
| 2010/0261799 A1 | 10/2010 | Vachon et al. |
| 2010/0273901 A1 | 10/2010 | Ehrenberg et al. |

* cited by examiner

Polymer T-3 Before and After Sulfonation

Polymer T-2 Before and After Sulfonation

Figure 3. Structure of films cast from: (left) 90/10 toluene/methanol, (center) 80/20 THF/toluene, and (right) 50/50 THF/toluene as imaged with AFM.
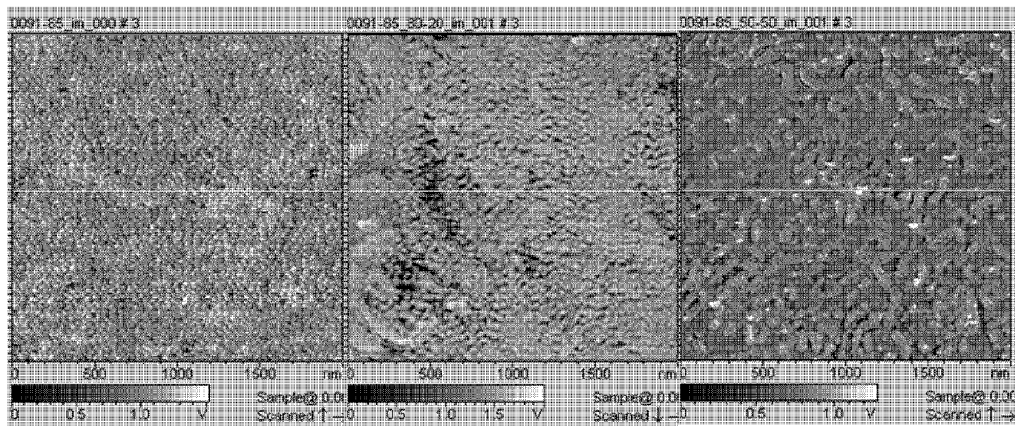
Figure 4. DSC plots showing differences in the melting of water as a function of casting solutions.
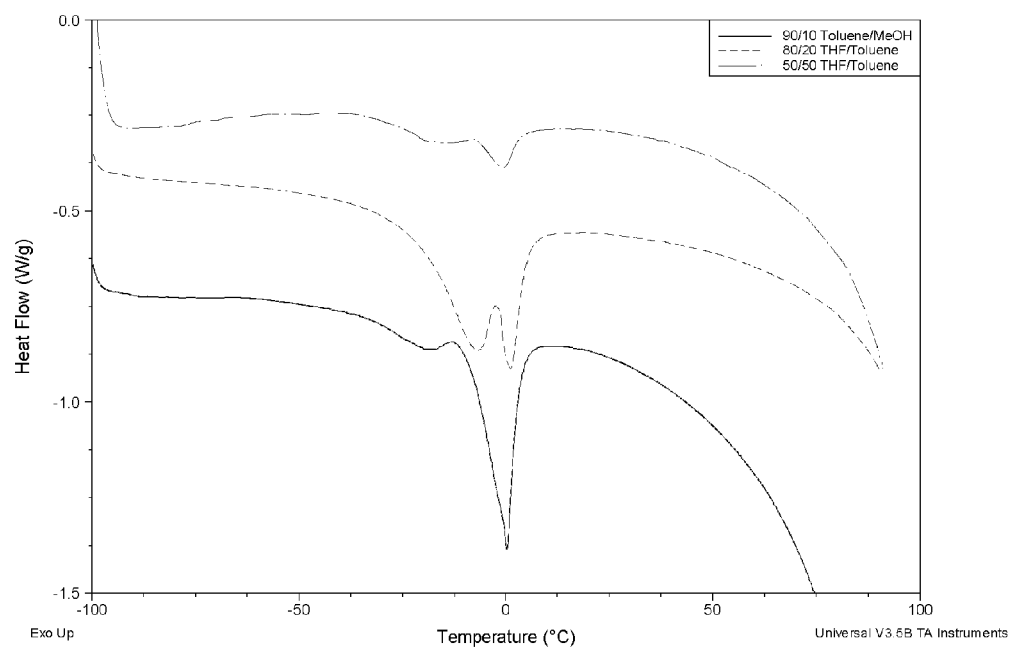

PROCESS FOR PREPARING SULFONATED BLOCK COPOLYMERS AND VARIOUS USES FOR SUCH BLOCK COPOLYMERS

CROSS-REFERENCE RELATED APPLICATIONS

This application is a divisional application of U.S. application Ser. No. 11/458,856 filed Jul. 20, 2006, the entire contents of which is hereby incorporated by reference, said U.S. application Ser. No. 11/458,856 claims priority to U.S. Provisional Application 60/701,768, the entire contents of which is hereby incorporated by reference.

FIELD OF THE INVENTION

The present invention relates to a process for preparing sulfonated block copolymers. In particular, the present invention relates to a process for preparing sulfonated block copolymers having at least two polymer end blocks that are resistant to sulfonation and at least one polymer interior block that is susceptible to sulfonation. The present invention further relates to the use of the inventive sulfonated block copolymers to prepare various articles or one or more parts of various articles.

BACKGROUND OF THE INVENTION

The preparation of styrene diene block copolymers ("SBC") is well known. In a representative synthetic method, an initiator compound is used to start the polymerization of one monomer. The reaction is allowed to proceed until all of the monomer is consumed, resulting in a living homopolymer. To this living homopolymer is added a second monomer that is chemically different from the first. The living end of the first polymer serves as the site for continued polymerization, thereby incorporating the second monomer as a distinct block into the linear polymer. The block copolymer so grown is living until terminated. Termination converts the living end of the block copolymer into a non-propagating species, thereby rendering the polymer non-reactive towards a monomer or coupling agent. A polymer so terminated is commonly referred to as a diblock copolymer. If the polymer is not terminated the living block copolymers can be reacted with additional monomer to form a sequential linear block copolymer. Alternatively, the living block copolymer can be contacted with multifunctional agents commonly referred to as coupling agents. Coupling two of the living ends together results in a linear triblock copolymer having twice the molecular weight of the starting, living, diblock copolymer. Coupling more than two of the living ends together results in a radial block copolymer architecture having at least three arms.

One of the first patents on linear ABA block copolymers made with styrene and butadiene is U.S. Pat. No. 3,149,182. These polymers in turn could be hydrogenated to form more stable block copolymers, such as those described in U.S. Pat. Nos. 3,595,942 and Re. 27,145. Selective hydrogenation to remove the C═C moieties in the polydiene segment of such polymers is critical in preparing block copolymers with good thermal and chemical resistance, particularly resistance to oxidative degradation.

Through the years, there have been many modifications made to such block copolymers to change and improve properties. One such modification has been to sulfonate the block copolymer. One of the first such sulfonated block copolymers is disclosed, for example, in U.S. Pat. No. 3,577,357 to Winkler. The resulting block copolymer was characterized as having the general configuration A-B-(B-A)1-5, wherein each A is a non-elastomeric sulfonated monovinyl arene polymer block and each B is a substantially saturated elastomeric alpha-olefin polymer block, said block copolymer being sulfonated to an extent sufficient to provide at least 1% by weight of sulfur in the total polymer and up to one sulfonated constituent for each monovinyl arene unit. The sulfonated polymers could be used as such, or could be used in the form of their acid, alkali metal salt, ammonium salt or amine salt. In the Winkler patent, a polystyrene-hydrogenated polyisoprene-polystyrene triblock copolymer was treated with a sulfonating agent comprising sulfur trioxide/triethyl phosphate in 1,2-dichloroethane. Such block copolymers exhibited water absorption characteristics that might be useful in water purification membranes and the like.

The sulfonation of unsaturated styrene-diene block copolymers is disclosed in O'Neill et al, U.S. Pat. No. 3,642,953. Polystyrene-polyisoprene-polystyrene was sulfonated using chloro-sulfonic acid in diethyl ether. Since the sulfonic acid functionality incorporated into the polymer promotes oxidation and the residual C═C sites left in the polymer backbone are prone to oxidation, these polymers had limited utility. As stated in column 3, line 38, of this patent: "The unsaturated block copolymer sulfonic acids obtained by this process are subject to rapid oxidative degradation in air, therefore, they must be handled under anaerobic conditions and/or stabilized with anti-oxidants until they have been cast from solution into their final form and converted to the more stable salt by neutralization or ion-exchange." The sulfonated, unsaturated block polymers prepared in the experiments outlined in the Examples of the O'Neill et al patent were cast as produced into thin films. The films exhibited excessive swelling (up to 1600% wt water uptake) and were weak. While the cast films could be stabilized by treatment with an excess of base and their properties did improve somewhat on neutralization (still only 300 to 500 psi of tensile strength); the films in the sulfonate salt form were now insoluble and could not be reshaped. Similarly, Makowski et al, U.S. Pat. No. 3,870,841 includes examples of sulfonation of a t-butylstyrene/isoprene random copolymer. As these sulfonated polymers have C═C sites in their backbone, they are not expected to be oxidatively stable in the sulfonic acid form either. Such polymers were used for applications requiring limited flexibility, and are not expected to have acceptable overall physical properties. Another sulfonated styrene/butadiene copolymer is disclosed in U.S. Pat. No. 6,110,616, Sheikh-Ali et al, where an SBR-type random copolymer is sulfonated.

Another route to make sulfonated block copolymers is disclosed in Balas et al, U.S. Pat. No. 5,239,010, where an acyl sulfate is reacted with a selectively hydrogenated block copolymer composed of at least one conjugated diene block and one alkenyl arene block. After hydrogenation, the block copolymer is modified by attaching sulfonic acid functional groups primarily in the alkenyl arene blocks (A blocks). The mechanical properties may be varied and controlled by varying the degree of functionalization (amount of sulfonation) and the degree of neutralization of the sulfonic acid groups to metal sulfonated salts.

In Pottick et al, U.S. Pat. No. 5,516,831, a blend of an aliphatic hydrocarbon oil and a functionalized, selectively hydrogenated block copolymer to which has been grafted sulfonic functional groups is disclosed. In the block copolymer of Pottick et al, substantially all of the sulfonic functional groups are grafted to the block copolymer on the alkenyl arene polymer block A, as opposed to the substantially completely, hydrogenated conjugated diene block copolymer B. Neutralization of the acid groups to a metal salt was preferred to prepare oil extended blends that retained substantial amounts of non-extended mechanical properties. The block copolymer blends were used for adhesives and sealants, as modifiers for lubricants, fuels and the like.

Recently there has been more attention given to the use of sulfonated block copolymers for fuel cells. For example, Ehrenberg et al, U.S. Pat. No. 5,468,574, discloses the use of a membrane comprising a graft copolymer of sulfonated styrene and butadiene. In the examples, an SEBS block copolymer (i.e., a selectively hydrogenated styrene/butadiene/styrene triblock copolymer) was sulfonated with sulfur trioxide to an extent of at least 25 mol percent basis the number of styrene units in the block copolymer. As shown in the patent, the sulfonic acid groups are all attached to the styrene units. The deleterious effects of water induced swelling in such membranes are discussed in the article by J. Won et al, titled "Fixation of Nanosized Proton Transport Channels in Membranes", Macromolecules, 2003, 36, 3228-3234 (Apr. 8, 2003). As disclosed in the Macromolecules article, a membrane was prepared by solvent casting a sample (from Aldrich) of a sulfonated (45 mol % basis styrene content) SEBS (Mw about 80,000, 28% w styrene) polymer onto glass. The membrane was immersed in water and found to absorb over 70% of its dry weight in water as a consequence of swelling. The rate of methanol transport through the water-swollen membrane was then tested and found to be undesirably high. This is not a preferred result for direct methanol fuel cell (DMFC) applications where segregation of methanol to only one compartment of the cell is essential for the device to generate electrical power. For these applications, "methanol crossover needs to be reduced, while maintaining proton conductivity and mechanical strength, to improve fuel cell performance." This problem was overcome to a certain extent, as described in the report by J. Won et. al, by first casting a film of a styrene-diene block copolymer, radiation crosslinking the film (cSBS), and then sulfonating the pre-formed article. While crosslinking the block copolymer prior to sulfonation overcame the problem of excessive swelling that was observed when an S-E/B-S polymer that was selectively sulfonated in the outer blocks was used to form a membrane, crosslinking technology is limited in its utility to thin, transparent articles that are readily penetrated by the radiation source. In addition, sulfonation of the crosslinked article is time consuming and uses an excess of dichloroethane (DCE). As reported by J. Won et. al, "The cSBS film was swollen in an excess amount of DCE overnight. The solution was heated to 50° C. and purged with nitrogen for 30 min. Then the acetyl sulfate solution (produced with the procedure described above) was added." "The solution was stirred for 4 h at this temperature, and then the reaction was terminated by the addition of 2-propanol, resulting in a sulfonated SBS crosslinked membrane (scSBS)." Cleaning up the sulfonated article was also problematic. "The membrane was washed in boiling water and many times with cold water. The complete removal of residual acid from the final product after sulfonation is important since it can interfere with the properties of the final product."

Still another type of block copolymer that has been sulfonated in the past is selectively hydrogenated styrene/butadiene block copolymers that have a controlled distribution interior block containing both styrene and butadiene, as opposed to the normal block copolymers that just contain butadiene in the interior block. Such block copolymers are disclosed in Published U.S. Patent Application Nos. 2003/0176582 and 2005/0137349, as well as PCT Published Application WO 2005/03812.

In the sulfonated block copolymers disclosed above, invariably the outer (hard) blocks are sulfonated due to the presence of styrene in the outer blocks. This means that upon exposure to water, hydration of the hard domains in the material will result in plasticization of those domains and significant softening. This softening of the hard domains results in a marked decrease in the mechanical integrity of membranes prepared from these block copolymers. Thus, there is a risk that when exposed to water any structure supported by these prior art sulfonated block copolymers will not have sufficient strength to maintain its shape. Hence, there are limits to how to use such a block copolymer and limits on its end use applications.

Other prior art sulfonated polymers are taught where the end blocks and interior blocks do not include hydrogenated dienes. U.S. Pat. No. 4,505,827 to Rose et al relates to a "water-dispersible" BAB triblock copolymer wherein the B blocks are hydrophobic blocks such as alkyl or sulfonated poly(t-butyl styrene) and the A blocks are hydrophilic blocks such as sulfonated poly(vinyl toluene). A key aspect of the polymers disclosed in Rose et al is that they must be "water dispersible", since the uses contemplated for the polymer are for drilling muds or for viscosity modification. Rose et al states at column 3, lines 51 to 52 that the polymer "exhibits hydrophobe association capabilities when dispersed in an aqueous medium." Rose et al. goes on to state in lines 53 to 56 that "[F]or purposes of the invention, such a polymer is one which, when mixed with water, the resulting mixture is transparent or translucent, and not milky white as in the case of a dispersion of a water-insoluble polymer." The polymer of Rose et al. is water-dispersible since the t-butyl styrene blocks are not large—typically the block copolymer will have less than 20 mole percent of B blocks, preferably from about 0.1 to about 2 mol percent. In addition, the B end blocks will likely contain a significant amount of sulfonation.

U.S. Pat. No. 4,492,785 to Valint et al. relates to "water soluble block polymers" which are viscosification agents for water. These water-soluble block copolymers are either diblock polymers of t-butyl styrene/metal styrene sulfonate or triblock polymers of t-butyl styrene/metal styrene sulfonate/t-butyl styrene. It appears from the structures and properties given that the interior block styrene is 100% sulfonated. This will result in the polymer being water-soluble. Further, in the structures given, each of the end blocks will comprise 0.25 to 7.5 mol percent of the polymer. With such a large interior block that is fully sulfonated, and has relatively small end blocks, the polymers will invariably be water-soluble.

None of the prior art references noted above disclose sulfonated polymers based on styrene and/or t-butyl styrene that are in a solid state in the presence of water and have both high water transport properties and sufficient wet strength. Accordingly, what is needed is a semi-permeable membrane with high water transport properties that maintains sufficient wet strength for a wide variety of applications.

SUMMARY OF THE INVENTION

It has now surprisingly been discovered that it is possible to achieve high water transport properties while maintaining sufficient wet strength for a wide variety of applications by using sulfonated block copolymers having one or more internal blocks that are susceptible to sulfonation and outer blocks that are resistant to sulfonation. These sulfonated saturated block copolymers of the present invention exhibit a balance of properties, including water transport, wet strength, dimensional stability and processability that have heretofore been unachievable. It has been discovered that when sulfonation is limited to one or more internal block(s) of the block copolymer, hydrophobicity of the outer blocks is retained, and hence their integrity in the presence of a hydrated center or rubber phase. The means by which sulfonation would be directed selectively to the internal or interior block is by, for example, the use of para substituted styrenic monomers such as para-tert-butylstyrene in the outer blocks. The large alkyl substituent at the para-position on the styrene ring reduces the reactivity of the ring towards sulfonation, thereby directing the sulfonation to one or more of the internal or interior block(s) of the polymer.

A key feature of sulfonated block copolymers having sulfonation resistant end blocks is that they can be formed into solid objects or articles which retain their solid character even in the presence of an excess of water. A solid is recognized as a material that does not flow under the stress of its own weight. The polymers of the present invention may be cast into solid membranes. While these membranes efficiently transport water vapor, they are solids even in the presence of an excess of water. The solid character of these membranes in water may be demonstrated by testing their resistance to flow under tensile stress while submerged in water. A simple tensile test, according to the methods outlined in ASTM D412, may be performed on the membrane while it is submerged in a bath of water; this measurement may be taken as a measure of the wet strength of the material. This test is usefully employed on a membrane that has been equilibrated in excess water. Materials that exhibit a wet tensile strength in excess of 100 pounds per square inch of cross sectional area are strong solids. Importantly, they are strong solids even in the presence of an excess of water. Clearly, such materials are not soluble in water. Water soluble materials will have no measurable strength when evaluated using the modified procedure of ASTM D412 which has been outlined above. Further, such materials are not dispersed in water. An aqueous dispersion of the polymer will have no measurable strength when tested using the modified procedure of ASTM D412 as discussed above. The polymer membranes of the present invention are not soluble in water and do not form dispersions when contacted with an excess of water. The newly discovered polymer membranes have good water vapor transport properties and have tensile strengths when equilibrated with water in excess of 100 psi. They are solids even when wet.

A distinguishing feature of the block copolymers of the present invention which have been selectively sulfonated in an interior block is that they can be formed into objects having a useful balance of properties that have heretofore been unachievable, including strength even when equilibrated with water, water vapor transport behavior, dimensional stability, and processability. The hydrophobic blocks and their position at the ends of the block copolymer chain contribute to the wet strength, dimensional stability and processability of these polymers and objects formed from them. The sulfonated block(s) positioned in the interior of the copolymer allow effective water vapor transport. The combined properties afford a unique material. As a result of the above, the sulfonated block copolymers of the present invention are capable of being utilized more effectively in a wide variety of uses in which the prior art sulfonated polymers proved deficient due to the weakness of such polymers in water. Note that sulfonated block copolymers that are "water soluble" or "water dispersed" by their nature would not have sufficient tensile strength for the applications disclosed herein.

Accordingly, the present invention broadly comprises sulfonated block copolymers for forming articles that are solids in water comprising at least two polymer end blocks and at least one saturated polymer interior block wherein
a. each end block is a polymer block resistant to sulfonation and each interior block is a saturated polymer block susceptible to sulfonation, said end and interior blocks containing no significant levels of olefinic unsaturation;
b. each end block independently having a number average molecular weight between about 1,000 and about 60,000 and each interior block independently having a number average molecular weight between about 10,000 and about 300,000;
c. said interior blocks being sulfonated to the extent of 10 to 100 mol percent; and
d. said sulfonated, block copolymer when formed into an article has a tensile strength greater than 100 psi in the presence of water according to ASTM D412.

Typically, in the sulfonated block copolymer, the mol percentage of end blocks will be sufficient such that the block copolymer will be insoluble in water and non-dispersible in water. In said block copolymer, the mol percent of the end blocks can be greater than 15%, preferably greater than 20%. In other instances, the mol percent of the end blocks can be greater than 20% and less than 70%, preferably greater than 20% and less than 50%. The hydrophobic units of the end blocks contribute to the block copolymer's insolubility. Furthermore, if the end block mol percent approaches the lower values, hydrophobicity of the entire block copolymer can be adjusted by incorporating hydrophobic monomer units into the interior blocks, including A blocks as well as B blocks.

Throughout the current application with regard to the present invention, the following terms have the following meanings. "Resistant to sulfonation" means that little, if any, sulfonation of the block occurs. "Susceptible to sulfonation" means that sulfonation is very likely to occur in the blocks referenced. The expression "resistant to sulfonation" as used with regard to the present invention with regard to end blocks and the expression "susceptible to sulfonation" with regard to the interior blocks are meant to express that sulfonation occurs primarily in the interior block(s) of the copolymer so that the degree of sulfonation which occurs in the interior block(s), relative to the total degree of sulfonation of the block copolymer, is in every instance, higher than the degree of sulfonation which occurs in the end blocks. The degree of sulfonation in the interior block(s) is at least 85% of the total overall sulfonation of the block copolymer. In alternative embodiments, the degree of sulfonation in the interior block(s) is at least 90% of the total sulfonation, with the preferred amount in this embodiment being at least 95% of the total sulfonation. In some embodiments, the end blocks may show no sulfonation. Note that throughout the specification there are discussions relating to end blocks and interior blocks. In many instances, the structures related to end blocks represented by "A" and interior blocks represented by "B" are used. Such discussions, unless indicated otherwise, are not intended to be limited to only those sulfonated block copolymers of the present invention that contain "A" end blocks and "B" interior blocks but are instead intended to be discussions that are representative of all structures of embodiments of the present invention in which end blocks that are resistant to sulfonation are represented by "A", "A1", or "A2" blocks and interior blocks that are susceptible to sulfonation are represented by "B", "B1", "B2", "D", "E" or "F" blocks. Furthermore, note that in some instances, more than one interior block may be susceptible to sulfonation. In those instances, the blocks may be the same or they may be different.

In addition, the term "containing no significant levels of unsaturation" means that the residual olefin unsaturation of the block copolymer is less than 2.0 milliequivalents of carbon-carbon double bonds per gram of polymer, preferably less than 0.2 milliequivalents of carbon-carbon double bonds per gram of block copolymer. This means, e.g., that for any conjugated diene polymer component present in said sulfonated block copolymer, that such conjugated diene must be hydrogenated such that at least 90% of the double bonds are reduced by the hydrogenation, preferably at least 95% of the double bonds are reduced by the hydrogenation, and even more preferably at least 98% of the double bonds are reduced by the hydrogenation. In one embodiment, the present invention broadly comprises sulfonated block copolymers comprising at least two polymer end blocks A and at least one polymer interior block B wherein a. each A block is a polymer block resistant to sulfonation and each B block is a polymer block susceptible to sulfonation, said A and B blocks containing no significant levels of olefinic unsaturation;

b. each A block independently having a number average molecular weight between about 1,000 and about 60,000 and each B block independently having a number average molecular weight between about 10,000 and about 300,000;

c. each A block comprising one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof, wherein any segments containing polymerized 1,3-cyclodiene or conjugated dienes are subsequently hydrogenated and wherein any A block comprising polymerized ethylene or hydrogenated polymers of a conjugated, acyclic diene have a melting point greater than 50° C., preferably greater than 80° C.;

d. each B block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

e. wherein said B blocks are sulfonated to the extent of 10 to 100 mol percent, based on the units of vinyl aromatic monomer in said B blocks;

f. the mol percent of vinyl aromatic monomers which are unsubstituted styrene monomers, ortho-substituted styrene monomers, meta-substituted styrene monomers, alpha-methylstyrene, 1,1-diphenylethylene and 1,2-diphenylethylene in each B block is between 10 mol percent and 100 mol percent; and g. said sulfonated block copolymer when formed into an article has a tensile strength greater than 100 psi in the presence of water according to ASTM D412.

In this embodiment, the A blocks may also contain up to 15 mol percent of monomers mentioned for the B blocks. Such sulfonated block copolymers of this embodiment may be represented by the structures A-B-A, (A-B-A)nX, (A-B)nX or mixtures thereof, where n is an integer from 2 to about 30, X is a coupling agent residue, and A and B are as defined hereinabove.

In another embodiment, the present invention relates to a sulfonated block copolymer comprising polymer blocks A1, A2, B1 and B2, having the structure (A1-B1-B2)nX, (A1-B2-B1)nX, (A2-B1-B2)nX, (A2-B2-B1)nX, (A1-A2-B1)nX, (A1-A2-B2)nX, (A2-A1-B1)nX, (A2-A1-B2)nX, (A1-A2-B1-B2)nX, (A1-A2-B2-B1)nX, (A2-A1-B1-B2)nX or (A2-A1-B2-B1)nX, where n is an integer from 2 to 30 and X is a coupling agent residue, and wherein:

a. each A1 block and each A2 block is a polymer block resistant to sulfonation and each B1 and each B2 block is a polymer block susceptible to sulfonation, said A1, A2, B1 and B2 blocks containing no significant levels of olefinic unsaturation;

b. each A1 block and each A2 block independently having a number average molecular weight between about 1,000 and about 60,000 and each B1 and B2 block independently having a number average molecular weight between about 10,000 and about 300,000;

c. each A1 block is selected from the group consisting of polymerized (i) ethylene, and (ii) conjugated dienes having a vinyl content less than 35 mol percent prior to hydrogenation wherein the conjugated dienes are subsequently hydrogenated;

d. each A2 block being selected from the group consisting of polymerized (i) para-substituted styrene monomers, and (ii) 1,3-cyclodiene monomers wherein the 1,3-cyclodiene monomers are subsequently hydrogenated;

e. each B1 block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

f. each B2 block being hydrogenated, copolymerized segments of at least one conjugated diene and at least one mono alkenyl arene selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

g. each B1 and each B2 block being sulfonated to the extent of 10 to 100 mol percent; and h. said sulfonated block copolymer when formed into an article has a tensile strength greater than 100 psi in the presence of water according to ASTM D412.

In still another aspect, the present invention includes sulfonated block copolymers also containing at least one block D having a glass transition temperature of less than 20° C. One such block comprises a hydrogenated polymer or copolymer of a conjugated diene selected from isoprene, 1,3-butadiene and mixtures thereof having a vinyl content prior to hydrogenation of between 20 and 80 mol percent and a number average molecular weight of between about 1000 and about 50,000. Another block D could comprise a polymer of an acrylate monomer or a silicone polymer having a number average molecular weight of between about 1000 and about 50,000. Another block D could be polymerized isobutylene having a number average molecular weight of between about 1,000 and about 50,000. In this embodiment, the present invention includes a sulfonated, block copolymer having the general configuration A-D-B-D-A, A-B-D-B-A, (A-D-B)nX, (A-B-D)nX, or mixtures thereof, where n is an integer from 2 to about 30, and X is coupling agent residue wherein:

a. each A block and each D block is a polymer block resistant to sulfonation and each B block is a polymer block susceptible to sulfonation, said A, B and D blocks containing no significant levels of olefinic unsaturation;

b. each A block independently having a number average molecular weight between about 1,000 and about 60,000, each D block independently having a number average molecular weight between about 1000 and about 50,000 and each B block independently having a number average molecular weight between about 10,000 and about 300,000;

c. each A block comprises one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof, wherein any segments containing polymerized 1,3-cyclodiene or conjugated dienes are subsequently hydrogenated;

d. each B block comprises segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

e. each D block comprises polymers having a glass transition temperature less than 20° C. and a number average molecular weight of between about 1,000 and about 50,000, said D block being selected from the group consisting of (i) a polymerized or copolymerized conjugated diene selected from isoprene, 1,3-butadiene having a vinyl content prior to hydrogenation of between 20 and 80 mol percent, (ii) a polymerized acrylate monomer, (iii) polymerized silicon, (iv) polymerized isobutylene and (v) mixtures thereof, wherein any segments containing polymerized 1,3-butadiene or isoprene are subsequently hydrogenated, and has a glass transition temperature of less than 20° C.;

f. wherein said B blocks are sulfonated to the extent of 10 to 100 mol percent, based on the units of vinyl aromatic monomer in said B blocks;

g. the mol percent of vinyl aromatic monomers which are unsubstituted styrene monomers, ortho-substituted styrene monomers, meta-substituted styrene monomers, alpha-methylstyrene, 1,1-diphenylethylene and 1,2-diphenylethylene in each B block being between 10 mol percent and 100 mol percent; and h. said sulfonated block copolymer when formed into an article has a tensile strength greater than 100 psi in the presence of water according to ASTM D412.

In a further alternative of this embodiment, the present invention includes sulfonated block copolymers which have more than one D block and in which the second D block is polymerized acrylate monomer or polymerized silicon polymer.

In a further embodiment, the present invention includes block copolymers for forming articles that are solids in water comprising at least two polymer end blocks A and at least one polymer interior block B wherein:

a. each A block is a polymer block containing essentially no sulfonic acid or sulfonate functional groups and each B block is a polymer block containing 10 to 100 mol percent sulfonic acid or sulfonate functional groups based on the number of monomer units of the B block, said A and B blocks containing no significant levels of olefinic unsaturation; and b. each A block independently having a number average molecular weight between about 1,000 and about 60,000 and each B block independently having a number average molecular weight between about 10,000 and about 300,000.

In a further embodiment of the present invention, the monomers comprising the B block directly above are sulfonic functional monomers. In a preferred embodiment, the monomers are selected from the group consisting of sodium p-styrenesulfonate, lithium p-styrenesulfonate, potassium p-styrenesulfonate, ammonium p-styrenesulfonate, amine p-styrenesulfonate, ethyl p-styrenesulfonate, sodium methallylsulfonate, sodium allylsulfonate, sodium vinylsulfonate and mixtures thereof.

In a still further aspect, the present invention relates to sulfonated block copolymers wherein a portion of the sulfonic functional groups have been neutralized with an ionizable metal compound to form metal salts.

An even further embodiment of the present invention comprises a sulfonated block copolymer comprising at least two polymer end blocks A, at least one polymer interior blocks E, and at least one polymer interior block F, having the structure A-E-F-E-A, A-F-E-F-A, (A-F-E)nX or (A-E-F)nX, where n is an integer from 2 to 30 and X is a coupling agent residue, and wherein:

a. each A block is a polymer block resistant to sulfonation and each E and F block is a polymer block susceptible to sulfonation, said A, E and F blocks containing no significant levels of olefinic unsaturation;

b. each A block independently having a number average molecular weight between about 1,000 and about 60,000 and each E and F block independently having a number average molecular weight between about 10,000 and about 300,000;

c. each A block comprises one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof, wherein any segments containing polymerized 1,3-cyclodiene or conjugated dienes are subsequently hydrogenated;

d. each F block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

e. each E block is a copolymerized hydrogenated block of at least one conjugated diene and at least one mono alkenyl arene selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

f. wherein said E and F blocks are sulfonated to the extent of 10 to 100 mol percent, based on the units of vinyl aromatic monomer in said E and F blocks; and g. said sulfonated block copolymer when formed into an article has a tensile strength greater than 100 psi in the presence of water according to ASTM D412.

In a preferred alternative to this embodiment, the A block is a polymer block of para-tert-butylstyrene, the F block is a polymer block of unsubstituted styrene, and the E block is a copolymer block of hydrogenated 1,3-butadiene and unsubstituted styrene.

Applicants also claim as their invention processes for making the sulfonated block copolymers of the present invention. One of the processes for preparing the sulfonated block copolymers comprises reacting a block copolymer with a sulfonation reagent that selectively sulfonates the B blocks of a block copolymer comprising at least two polymer end blocks A and at least one polymer interior block B wherein:

a. each A block is a polymer block resistant to sulfonation and each B block is a polymer block susceptible to sulfonation, said A and B blocks containing no significant levels of olefinic unsaturation;
b. each A block independently having a number average molecular weight between about 1,000 and about 60,000 and each B block independently having a number average molecular weight between about 10,000 and about 300,000, wherein the mole percent of A end blocks is 20 to 50 percent;
c. said B blocks are sulfonated to the extent of 10 to 100 mol percent; and
d. said sulfonated block copolymer having a tensile strength greater than 100 psi in the presence of water according to ASTM D412.

Another process comprises preparing sulfonated block copolymers for forming articles that are solids in water having at least two polymer end blocks A and at least one polymer interior block B, the process comprising sulfonating said interior block B until said block B is substantially sulfonated, and wherein:

a. each said A block is other than solely polymers of ethylene or solely hydrogenated polymers of conjugated dienes;
b. wherein said block copolymer is water insoluble; and
c. wherein said end blocks A have essentially no sulfonated monomers.

In one particularly preferred embodiment of the present invention, the sulfonation agent utilized is an acyl sulfate, and in a particularly preferred alternative embodiment, the sulfonation agent utilized is sulfur trioxide.

Any number of precursor molecules may be utilized in the preparation of the sulfonated block copolymers of the present invention. In one preferred embodiment of the present invention, the precursor block copolymer, prior to hydrogenation, has the general configuration A-B-A, (A-B-A)nX, (A-B)nX, A-D-B-D-A, A-B-D-B-A, (A-D-B)nX, (A-B-D)nX or mixtures thereof, where n is an integer from 2 to about 30, and X is a coupling agent residue and wherein:

a. each A block is a polymer block resistant to sulfonation, each D block is a polymer block resistant to sulfonation, and each B block is a polymer block susceptible to sulfonation, said A, D and B blocks containing no significant levels of olefinic unsaturation;
b. each A block independently having a number average molecular weight between about 1,000 and about 60,000, each D block independently having a number average molecular weight between about 1,000 and about 50,000, and each B block independently having a number average molecular weight between about 10,000 and about 300,000;
c. each A block comprises one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof;
d. each B block comprises segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;
e. each D block comprises polymers having a glass transition temperature less than 20° C. and a number average molecular weight of between about 1000 and about 50,000, said D block being selected from the group consisting of (i) a polymerized or copolymerized conjugated diene selected from isoprene, 1,3-butadiene having a vinyl content prior to hydrogenation of between 20 and 80 mol percent, (ii) a polymerized acrylate monomer, (iii) polymerized silicon, (iv) polymerized isobutylene and (v) mixtures thereof, wherein any segments containing polymerized 1,3-butadiene or isoprene are subsequently hydrogenated; and
f. the mol percent of vinyl aromatic monomers which are unsubstituted styrene monomers, ortho-substituted styrene monomers, meta-substituted styrene monomers, alpha-methylstyrene, 1,1-diphenylethylene and 1,2-diphenylethylene in each B block is between 10 mol percent and 100 mol percent.

In another preferred embodiment of the present invention, the precursor block copolymer, prior to hydrogenation, has the general configuration (A1-B1-B2)nX, (A1-B2-B1)nX, (A2-B1-B2)nX, (A2-B2-B1)nX, (A1-A2-B1)nX, (A1-A2-B2)nX, (A2-A1-B1)nX, (A2-A1-B2)nX, (A1-A2-B1-B2)nX, (A1-A2-B2-B1)nX, (A2-A1-B1-B2)nX or (A2-A1-B2-B1)nX, where n is an integer from 2 to 30 and X is a coupling agent residue, and wherein:

a. each A1 block and each A2 block is a polymer block resistant to sulfonation and each B1 and each B2 block is a polymer block susceptible to sulfonation, said A1, A2, B1 and B2 blocks containing no significant levels of olefinic unsaturation;
b. each A1 block and each A2 block independently having a number average molecular weight between about 1,000 and about 60,000 and each B1 and B2 block independently having a number average molecular weight between about 10,000 and about 300,000;
c. each A1 block is selected from the group consisting of polymerized (i) ethylene, and (ii) conjugated dienes having a vinyl content less than 35 mol percent prior to hydrogenation;
d. each A2 block being selected from the group consisting of polymerized (i) para-substituted styrene monomers, and (ii) 1,3-cyclodiene monomers;
e. each B1 block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;
f. each B2 block being polymerized segments of at least one conjugated diene and at least one mono alkenyl arene selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;
and
g. each B1 and each B2 block is sulfonated to the extent of 10 to 100 mol percent.

Still another class of precursors include those of the general configuration A-E-F-E-A or (A-E-F)nX, where n is an integer from 2 to 30 and X is a coupling agent residue, and wherein:

a. each A block is a polymer block resistant to sulfonation and each E and F block is a polymer block susceptible to sulfonation, said A, E and F blocks containing no significant levels of olefinic unsaturation;
b. each A block independently having a number average molecular weight between about 1,000 and about 60,000 and each E and F block independently having a number average molecular weight between about 10,000 and about 300,000;
c. each A block being selected from the group consisting of polymerized (i) para-substituted styrene monomers;
d. each F block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;
e. each E block is a polymerized block of at least one conjugated diene and at least one mono alkenyl arene selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;
and
f. wherein said E and F blocks are sulfonated to the extent of 10 to 100 mol percent, based on the units of vinyl aromatic monomer in said E and F blocks.

Those of ordinary skill in the art will recognize that the above noted structures listed are not necessarily intended to be an exhaustive list of possible precursors for preparing the block copolymers of the present invention. The above precursors can be used as the starting materials in the process for preparing the sulfonated block copolymers of the present invention utilizing the process set forth hereinbefore as well as any other process that is readily available in the art provided that the final product meets the requirements of the present invention. These requirements include that the sulfonated block copolymer be a solid in the presence of water, the interior block(s) contain one or more sulfonic functional groups after sulfonation and the sulfonated block copolymer when formed into an article has a tensile strength greater than 100 psi in the presence of water according to ASTM D412.

In still another aspect, the present invention comprises an article formed at least in part from a composition comprising the inventive sulfonated block copolymer. In particular, the present invention contemplates articles, such as, for example, fuel cells, proton exchange membranes for fuel cells, dispersions of metal impregnated carbon particles in sulfonated polymer cement for use in an electrode assemblies, including electrode assemblies for fuel cells, fabrics, coated fabrics, surgical supplies and devices, filtration membranes, air conditioning membranes, heat recovery membranes, desalination membranes, adhesives, personal hygiene articles, super absorbent articles, binders for super absorbents and antifouling coatings. Specific examples of such articles include, but are not limited to, selective, permeability membranes formed in part from a composition comprising the sulfonated block copolymer. Other uses include fibers, tubes, fabrics, sheets, coatings for woven and non-woven fabrics and laminates. Specific applications include, but are not limited to, breathable protective clothing and gloves for first responders, firefighters, chemical and biological workers, agricultural workers, medical employees, and military personnel involved in handling potentially hazardous materials; sports and recreational clothing; tenting; selective membranes for industrial, medical and water purification applications; and systems which avoid moisture build up inside the walls and between the floor and foundation of a house. Other specific applications are in personal hygiene, including use as super absorbents or binders for super absorbents in diapers or incontinence products. Still other specific applications include marine coatings and anti-fouling coatings in general. Yet other applications include coatings for membranes, such as coatings on polysulfone desalination membranes.

In yet another aspect, the present invention includes a fuel cell incorporating one or more membranes made from the sulfonated block copolymers of the present invention. More specifically, the present invention includes a fuel cell comprising:
a. a membrane made from the sulfonated block copolymer;
b. first and second opposed electrodes in contact with said membrane;
c. means for supplying a fuel to said first electrode; and
d. means for permitting an oxidant to contact said second electrode.

Without wishing to be bound to a particular theory, the inventors believe that the significance of the present invention depends upon two structural features of the block copolymers: 1) the striking polarity differences between the outer A blocks and the interior B blocks regulate the physics a) of phase separation of the blocks of the copolymers, b) of water transportation through the membranes, and c) of the barrier properties of these polymers to species other than water and protons; and 2) the strength and dimensional stability of materials prepared from these polymers depends on the A blocks having no or very little functionality. The polarity of the B interior blocks derives from the sulfonation of the vinyl aromatic moieties enchained in the B interior block segments(s). In the solid phase, these aromatic sulfonic acid species ($-SO3H$ centers) self assemble into a continuous, polar phase that is extremely hydrophilic. This phase affords a ready pathway for protons or water to pass from one side of the membrane to the other. The greater is the density of $-SO3H$ sites in this phase (mol of $-SO3H/g$ of block copolymer), the faster is the transport of water molecules through the composite material. These pathways might be thought of as microphase separated ion or water channels that are approximately ten to a few thousand angstroms wide. In this multi-phase material, these channels are constrained by a non-polar, hydrophobic phase, which is composed of the hydrophobic A blocks of the copolymer. As the A blocks contain no or very few reactive centers, following sulfonation the A blocks have no or very little sulfonic acid functionality. As a result and in contrast to the B interior blocks, the A blocks are very resistant to permeation by water or protonic species. The properties of the A block phase of the multiphasic material are not readily affected by the addition of protonic materials or water. For this reason, the non-polar A block phase of the copolymer material is not significantly weakened by the addition of water. By example with regard to one embodiment of the present invention, as each B interior block is chemically attached to two A block outer segments, the composite, multiphasic material has substantial strength in the wet state, as well. In fact, a comparison of the strength of a film or membrane prepared from a selectively sulfonated block copolymer tested while wet versus its strength when tested while dry is a good measure of the absence (or near absence) of functionality in the A block of the copolymer; the wet strength should be at least more than 30% of the strength of the dry sample.

Furthermore, the non-polar, hydrophobic phase may be continuous affording a co-continuous multi-phase structure.

When this is the case, the strength of this phase and its resistance to swelling in the presence of water, controls and limits the level of swelling that can occur in the hydrophilic phase. In this way, the dimensional stability of the fabricated part is controlled. Even if the hydrophobic A block phase is dispersed, the strength of that phase constrains the swelling of the hydrophilic phase to the limit defined by the extendibility of the sulfonated B blocks in water. As the ends of the B blocks are tethered to A blocks that are not plasticized by water, they can only swell to the extent defined by their chain length. Swelling cannot overcome the strength of the chemical bond that holds the A and B blocks (outer and interior blocks) together.

The material properties—hardness, strength, rigidity, and temperature resistance—of composites prepared from these block copolymers will be strongly affected by the nature of the A block polymer(s) and the continuity, or lack thereof, of the hydrophobic phase. On the other hand, the water and proton transport properties, elasticity, flexibility, and toughness of these materials will be strongly affected by the nature of the B block polymer or copolymer of the multi-phase material. Depending upon the choice of monomer(s) used in making the interior segment of the block copolymer, the selectively, sulfonated, block copolymer may afford a very elastic and soft material, or a very tough but stiff material can be formed. As water acts to plasticize the interactions of the sulfonated moieties in the hydrophilic phase, the addition of water to these composites will tend to soften them--to make them less stiff The barrier properties of these materials are affected by the properties of both the hydrophilic and hydrophobic phases of the composite. The permeation of non-polar gases and non-polar liquids is greatly restricted by the high polarity and cohesive energy of the hydrophilic phase. Also, the hydrophilic phase must be continuous or co-continuous. The hydrophobic phase optionally may not be continuous in which case there is no continuity for the flow of molecules through the non-polar phase. When the hydrophobic phase is co-continuous with the ion channels, the density (non-porous solid) of the hydrophobic phase impedes the diffusion molecules through that phase of the material.

Block copolymers having sulfonation resistant outer segments, A blocks, and sulfonation susceptible interior segments, saturated B blocks, may be selectively sulfonated to afford materials having a unique two-phase structure. A consequence of this structure is that non-crosslinked polymers having a unique balance of useful properties—good dimensional stability, surprising water transport rates, and surprising strength in the presence of water—may be formed. The specific balance of properties needed for a particular application may be tuned by adjusting the nature or dimensions of the A and B blocks of the copolymer, the level of sulfonation of the polymer, the linearity or degree of branching in the starting polymer before sulfonation, and the amount of neutralization, if any, of the —SO3H sites. The need for materials having these types of properties is great. Myriad applications for films, membranes, fibers to include non-woven fibers, coatings, adhesives, molded articles and the like have been identified. The use of these articles to provide protection against chemical and biological agents, to purify aqueous streams, to guard against fungal and microbial growth, to allow evaporative cooling by transport of water (particularly from sweating) to a surface, to enhance the absorption of radiant energy when wet, and to soak up water are envisioned. The breadth of utility of this invention therefore appears to be large.

BRIEF DESCRIPTION OF THE DRAWING

FIG. 3 shows the structure of films cast from: (left) 90/10 toluene/methanol, (center) 80/20 THF/toluene, and (right) 50/50 THF/toluene as imaged with AFM.

FIG. 4 displays DSC plots showing differences in the melting of water as a function of casting solutions.

DETAILED DESCRIPTION OF THE INVENTION

Figure 1:
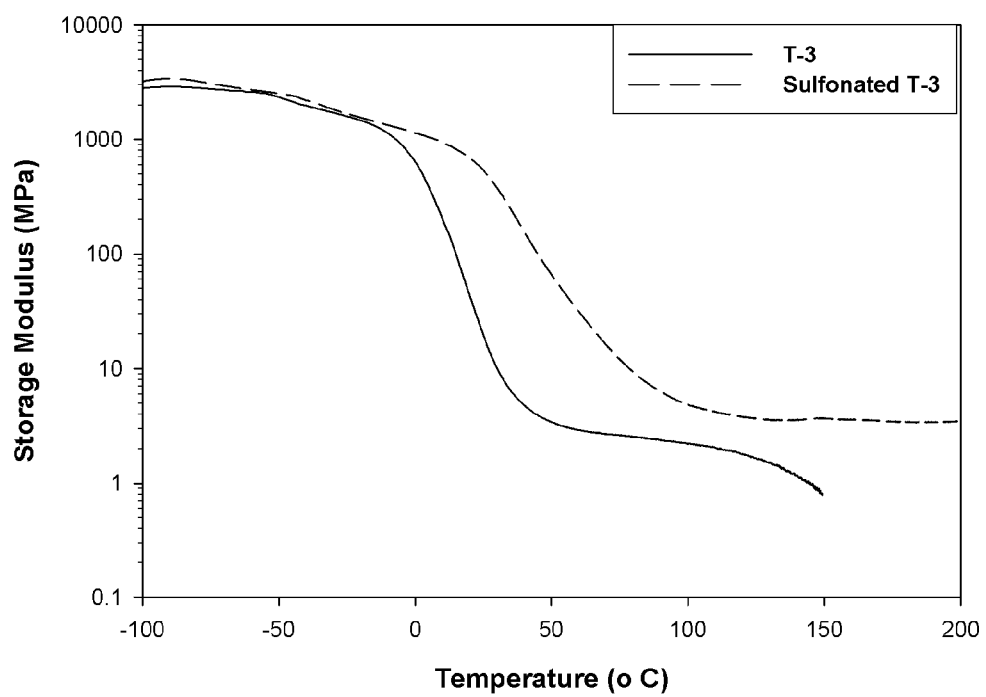
FIG. 1 shows a comparison of the storage modulus of sample T-3 before and after sulfonation. This figure shows that the midpoint of the glass to rubber transition, Tg, of the S/EB interior block moves from approximately 15° C. to approximately 50° C.

The base polymers needed to prepare the sulfonic acid containing block copolymers of the present invention may be made by a number of different processes, including anionic polymerization, moderated anionic polymerization, cationic polymerization, Ziegler-Natta polymerization, and living or stable free radical polymerization. Anionic polymerization is described below in the detailed description, and in the patents referenced. Moderated anionic polymerization processes for making styrenic block copolymers have been disclosed, for example, in U.S. Pat. Nos. 6,391,981, 6,455,651 and 6,492,469, each incorporated herein by reference. Cationic polymerization processes for preparing block copolymers are disclosed, for example, in U.S. Pat. Nos. 6,515,083 and 4,946,899, each incorporated herein by reference. Living Ziegler-Natta polymerization processes that can be used to make block copolymers were recently reviewed by G. W. Coates, P. D. Hustad, and S. Reinartz in Angew. Chem. Int. Ed., 2002, 41, 2236-2257; a subsequent publication by H. Zhang and K. Nomura (JACS Communications, 2005) describes the use of living Z-N techniques for making styrenic block copolymers specifically. The extensive work in the field of nitroxide mediated living radical polymerization chemistry has been reviewed; see C. J. Hawker, A. W. Bosman, and E. Harth, Chemical Reviews, 101(12), pp. 3661-3688 (2001). As outlined in this review, styrenic block copolymers could be made using living or stable free radical techniques. For the polymers of the present invention, nitroxide mediated polymerization methods will be the preferred living or stable free radical polymerization process.

1. Polymer Structure

One of the important aspects of the present invention relates to the structure of the sulfonated block copolymers. In one embodiment, these block copolymers made by the present invention will have at least two polymer end or outer blocks A and at least one saturated polymer interior block B wherein each A block is a polymer block resistant to sulfonation and each B block is a polymer block susceptible to sulfonation.

Preferred structures have the general configuration A-B-A, (A-B)n(A), (A-B-A)n, (A-B-A)nX, (A-B)nX, A-B-D-B-A, A-D-B-D-A, (A-D-B)n(A), (A-B-D)n(A), (A-B-D)nX, (A-D-B)nX or mixtures thereof, where n is an integer from 2 to about 30, X is coupling agent residue and A, B and D are as defined hereinbefore.

Most preferred structures are either the linear A-B-A, (A-B)2X, (A-B-D)nX 2X and (A-D-B)nX 2X structures or the radial structures (A-B)nX and (A-D-B)nX where n is 3 to 6. Such block copolymers are typically made via anionic polymerization, cationic polymerization or Ziegler-Natta polymerization. Preferably, the block copolymers are made via anionic polymerization. It is recognized that in any polymerization, the polymer mixture will include a certain amount of A-B diblock copolymer, in addition to any linear and/or radial polymers.

The A blocks are one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof. If the A segments are polymers of 1,3-cyclodiene or conjugated dienes, the segments will be hydrogenated subsequent to polymerization.

The para-substituted styrene monomers are selected from para-methylstyrene, para-ethylstyrene, para-n-propylstyrene, para-iso-propylstyrene, para-n-butylstyrene, para-sec-butylstyrene, para-iso-butylstyrene, para-t-butylstyrene, isomers of para-decylstyrene, isomers of para-dodecylstyrene and mixtures of the above monomers. Preferred para-substituted styrene monomers are para-t-butylstyrene and para-methylstyrene, with para-t-butylstyrene being most preferred. Monomers may be mixtures of monomers, depending on the particular source. It is desired that the overall purity of the para-substituted styrene monomers be at least 90% wt, preferably at least 95% wt, and even more preferably at least 98% wt of the desired para-substituted styrene monomer.

When the A blocks are polymers of ethylene, it may be useful to polymerize ethylene via a Ziegler-Natta process, as taught in the references in the review article by G. W. Coates et. al, as cited above, which disclosure is herein incorporated by reference. It is preferred to make the ethylene blocks using anionic polymerization techniques as taught in U.S. Pat. No. 3,450,795, which disclosure is herein incorporated by reference. The block molecular weight for such ethylene blocks will typically be between about 1,000 and about 60,000.

When the A blocks are polymers of alpha olefins of 3 to 18 carbon atoms, such polymers are prepared by via a Ziegler-Natta process, as taught in the references in the review article by G. W. Coates et. al, as cited above, which disclosure is herein incorporated by reference. Preferably the alpha olefins are propylene, butylene, hexane or octene, with propylene being most preferred. The block molecular weight for such alpha olefin blocks will typically be between about 1,000 and about 60,000.

When the A blocks are hydrogenated polymers of 1,3-cyclodiene monomers, such monomers are selected from the group consisting of 1,3-cyclohexadiene, 1,3-cycloheptadiene and 1,3-cyclooctadiene. Preferably, the cyclodiene monomer is 1,3-cyclohexadiene. Polymerization of such cyclodiene monomers is disclosed in U.S. Pat. No. 6,699,941, which disclosure is herein incorporated by reference. It will be necessary to hydrogenate the A blocks when using cyclodiene monomers since unhydrogenated polymerized cyclodiene blocks would be susceptible to sulfonation.

When the A blocks are hydrogenated polymers of conjugated acyclic dienes having a vinyl content less than 35 mol percent prior to hydrogenation, it is preferred that the conjugated diene is 1,3-butadiene. It is necessary that the vinyl content of the polymer prior to hydrogenation be less than 35 mol percent, preferably less than 30 mol percent. In certain embodiments, the vinyl content of the polymer prior to hydrogenation will be less than 25 mol percent, even more preferably less than 20 mol percent, and even less than 15 mol percent with one of the more advantageous vinyl contents of the polymer prior to hydrogenation being less than 10 mol percent. In this way, the A blocks will have a crystalline structure, similar to that of polyethylene. Such A block structures are disclosed in U.S. Pat. Nos. 3,670,054 and 4,107,236, which disclosures are herein incorporated by reference.

The A blocks may also be polymers of acrylic esters or methacrylic esters. These polymer blocks may be made according to the methods disclosed in U.S. Pat. No. 6,767,976, which disclosure is herein incorporated by reference. Specific examples of the methacrylic ester include esters of a primary alcohol and methacrylic acid, such as methyl methacrylate, ethyl methacrylate, propyl methacrylate, n-butyl methacrylate, isobutyl methacrylate, hexyl methacrylate, 2-ethylhexyl methacrylate, dodecyl methacrylate, lauryl methacrylate, methoxyethyl methacrylate, dimethylaminoethyl methacrylate, diethylaminoethyl methacrylate, glycidyl methacrylate, trimethoxysilylpropyl methacrylate, trifluoromethyl methacrylate, trifluoroethyl methacrylate; esters of a secondary alcohol and methacrylic acid, such as isopropyl methacrylate, cyclohexyl methacrylate and isobornyl methacrylate; and esters of a tertiary alcohol and methacrylic acid, such as tert-butyl methacrylate. Specific examples of the acrylic ester include esters of a primary alcohol and acrylic acid, such as methyl acrylate, ethyl acrylate, propyl acrylate, n-butyl acrylate, isobutyl acrylate, hexyl acrylate, 2-ethylhexyl acrylate, dodecyl acrylate, lauryl acrylate, methoxyethyl acrylate, dimethylaminoethyl acrylate, diethylaminoethyl acrylate, glycidyl acrylate, trimethoxysilylpropyl acrylate, trifluoromethyl acrylate, trifluoroethyl acrylate; esters of a secondary alcohol and acrylic acid, such as isopropyl acrylate, cyclohexyl acrylate and isobornyl acrylate; and esters of a tertiary alcohol and acrylic acid, such as tert-butyl acrylate. If necessary, as raw material or raw materials, one or more of other anionic polymerizable monomers may be used together with the (meth)acrylic ester in the present invention. Examples of the anionic polymerizable monomer that can be optionally used include methacrylic or acrylic monomers such as trimethylsilyl methacrylate, N-isopropylmethacrylamide, N-tert-butylmethacrylamide, trimethylsilyl acrylate, N-isopropylacrylamide, and N-tert-butylacrylamide. Moreover, there may be used a multifunctional anionic polymerizable monomer having in the molecule thereof two or more methacrylic or acrylic structures, such as methacrylic ester structures or acrylic ester structures (for example, ethylene glycol diacrylate, ethylene glycol dimethacrylate, 1,4-butanediol diacrylate, 1,4-butanediol dimethacrylate, 1,6-hexanediol diacrylate, 1,6-hexanediol dimethacrylate, trimethylolpropane triacrylate and trimethylolpropane trimethacrylate).

In the polymerization processes used to make the acrylic or methacrylic ester polymer blocks, only one of the monomers, for example, the (meth)acrylic ester may be used, or two or more thereof may be used in combination. When two or more of the monomers may be used in combination, any copolymerization form selected from random, block, tapered block and the like copolymerization forms may be effected by selecting conditions such as a combination of the monomers and the timing of adding the monomers to the polymerization system (for example, simultaneous addition of two or more monomers, or separate additions at intervals of a given time).

The A blocks may also contain up to 15 mol percent of the vinyl aromatic monomers mentioned for the B blocks. In some embodiments, the A blocks may contain up to 10 mol percent, preferably they will contain only up to 5 mol percent, and particularly preferably only up to 2 mol percent of the vinyl aromatic monomers mentioned in the B blocks. However, in the most preferred embodiments, the A blocks will contain no vinyl monomers mentioned in the B blocks. Accordingly, the sulfonation level in the A blocks may be from 0 up to 15 mol percent of the total monomers in the A block. Note that the ranges can include all combinations of mol percents listed herewith.

With regard to the saturated B blocks, each B block comprises segments of one or more polymerized vinyl aromatic monomers selected from unsubstituted styrene monomer, ortho-substituted styrene monomers, meta-substituted styrene monomers, alpha-methylstyrene monomer, 1,1-diphenylethylene monomer, 1,2-diphenylethylene monomer, and mixtures thereof. In addition to the monomers and polymers noted immediately before, the B blocks may also comprise a hydrogenated copolymer of such monomer (s) with a conjugated diene selected from 1,3-butadiene, isoprene and mixtures thereof, having a vinyl content of between 20 and 80 mol percent. These copolymers with hydrogenated dienes may be random copolymers, tapered copolymers, block copolymers or controlled distribution copolymers. Accordingly, there are two preferred structures: one in which the B blocks are hydrogenated and comprise a copolymer of conjugated dienes and the vinyl aromatic monomers noted in this paragraph, and another in which the B blocks are unsubstituted styrene monomer blocks which are saturated by virtue of the nature of the monomer and do not require the added process step of hydrogenation. The B blocks having a controlled distribution structure are disclosed in U.S. Published Patent Application No. 2003/0176582, which disclosure is herein incorporated by reference. U.S. Published Patent Application No. 2003/0176582 also discloses the preparation of sulfonated block copolymers, albeit not the structures claimed in the present invention. The B blocks comprising a styrene block are described herein. In one preferred embodiment, the saturated B blocks are unsubstituted styrene blocks, since the polymer will not then require a separate hydrogenation step.

In addition, another aspect of the present invention is to include at least one impact modifier block D having a glass transition temperature less than 20° C. One such example of an impact modifier block D comprises a hydrogenated polymer or copolymer of a conjugated diene selected from isoprene, 1,3-butadiene and mixtures thereof having a vinyl content prior to hydrogenation of between 20 and 80 mol percent and a number average molecular weight of between 1,000 and 50,000. Another example would be an acrylate or silicone polymer having a number average molecular weight of 1,000 to 50,000. In still another example, the D block would be a polymer of isobutylene having a number average molecular weight of 1,000 to 50,000.

Each A block independently has a number average molecular weight between about 1,000 and about 60,000 and each B block independently has a number average molecular weight between about 10,000 and about 300,000. Preferably each A block has a number average molecular weight of between 2,000 and 50,000, more preferably between 3,000 and 40,000 and even more preferably between 3,000 and 30,000. Preferably each B block has a number average molecular weight of between 15,000 and 250,000, more preferably between 20,000 and 200,000, and even more preferably between 30,000 and 100,000. Note that the ranges can also include all combinations of said number average molecular weights listed herewith. These molecular weights are most accurately determined by light scattering measurements, and are expressed as number average molecular weight. Preferably, the sulfonated polymers have from about 8 mol percent to about 80 mol percent, preferably from about 10 to about 60 mol percent A blocks, more preferably more than 15 mol percent A blocks and even more preferably from about 20 to about 50 mol percent A blocks.

The relative amount of vinyl aromatic monomers which are unsubstituted styrene monomer, ortho-substituted styrene monomer, meta-substituted styrene monomer, alpha-methylstyrene monomer, 1,1-diphenylethylene monomer, and 1,2-diphenylethylene monomer in the sulfonated block copolymer is from about 5 to about 90 mol percent, preferably from about 5 to about 85 mol percent. In alternative embodiments, the amount is from about 10 to about 80 mol percent, preferably from about 10 to about 75 mol percent, more preferably from about 15 to about 75 mol percent, with the most preferred being from about 25 to about 70 mol percent. Note that the ranges can include all combinations of mol percents listed herewith.

As for the saturated B block, in one preferred embodiment the mol percent of vinyl aromatic monomers which are unsubstituted styrene monomer, ortho-substituted styrene monomer, meta-substituted styrene monomer, alpha-methylstyrene monomer, 1,1-diphenylethylene monomer, and 1,2-diphenylethylene monomer in each B block is from about 10 to about 100 mol percent, preferably from about 25 to about 100 mol percent, more preferably from about 50 to about 100 mol percent, even more preferably from about 75 to about 100 mol percent and most preferably 100 mol percent. Note that the ranges can include all combinations of mol percents listed herewith.

As for the level of sulfonation, typical levels are where each B block contains one or more sulfonic functional groups. Preferred levels of sulfonation are 10 to 100 mol percent based on the mol percent of vinyl aromatic monomers which are unsubstituted styrene monomer, ortho-substituted styrene monomer, meta-substituted styrene monomer, alpha-methylstyrene monomer, 1,1-diphenylethylene monomer, and 1,2-diphenylethylene monomer in each B block, more preferably about 20 to 95 mol percent and even more preferably about 30 to 90 mol percent. Note that the range of sulfonation can include all combinations of mol percents listed herewith. The level of sulfonation is determined by titration of a dry polymer sample, which has been redissolved in tetrahydrofuran with a standardized solution of NaOH in a mixed alcohol and water solvent.

2. Overall Anionic Process to Prepare Polymers

With regard to the process to prepare the polymers, the anionic polymerization process comprises polymerizing the suitable monomers in solution with a lithium initiator. The solvent used as the polymerization vehicle may be any hydrocarbon that does not react with the living anionic chain end of the forming polymer, is easily handled in commercial polymerization units, and offers the appropriate solubility characteristics for the product polymer. For example, non-polar aliphatic hydrocarbons, which are generally lacking in ionizable hydrogen atoms make particularly suitable solvents. Frequently used are cyclic alkanes, such as cyclopentane, cyclohexane, cycloheptane, and cyclooctane, all of which are relatively non-polar. Other suitable solvents will be known to those skilled in the art and can be selected to perform effectively in a given set of process conditions, with polymerization temperature being one of the major factors taken into consideration.

Starting materials for preparing the block copolymers of the present invention include the initial monomers noted above. Other important starting materials for anionic co polymerizations include one or more polymerization initiators. In the present invention such include, for example, alkyl lithium compounds such as s-butyllithium, n-butyllithium, t-butyllithium, amyllithium and the like and other organo lithium compounds including di-initiators such as the di-sec-butyl lithium adduct of m-diisopropenyl benzene. Other such di-initiators are disclosed in U.S. Pat. No. 6,492,469, each incorporated herein by reference. Of the various polymerization initiators, s-butyllithium is preferred. The initiator can be used in the polymerization mixture (including monomers and solvent) in an amount calculated on the basis of one initiator molecule per desired polymer chain. The lithium initiator process is well known and is described in, for example, U.S. Pat. Nos. 4,039,593 and Re. 27,145, which descriptions are incorporated herein by reference.

Polymerization conditions to prepare the block copolymers of the present invention are typically similar to those used for anionic polymerizations in general. In the present invention polymerization is preferably carried out at a temperature of from about −30° C. to about 150° C., more preferably about 10° C. to about 100° C., and most preferably, in view of industrial limitations, from about 30° C. to about 90° C. The polymerization is carried out in an inert atmosphere, preferably nitrogen, and may also be accomplished under pressure within the range of from about 0.5 to about 10 bars. This copolymerization generally requires less than about 12 hours, and can be accomplished in from about 5 minutes to about 5 hours, depending upon the temperature, the concentration of the monomer components, and the molecular weight of the polymer that is desired. When two or more of the monomers are used in combination, any copolymerization form selected from random, block, tapered block, controlled distribution block, and the like copolymerization forms may be utilized.

It is recognized that the anionic polymerization process could be moderated by the addition of a Lewis acid, such as an aluminum alkyl, a magnesium alkyl, a zinc alkyl or combinations thereof. The affects of the added Lewis acid on the polymerization process are 1) to lower the viscosity of the living polymer solution allowing for a process that operates at higher polymer concentrations and thus uses less solvent, 2) to enhance the thermal stability of the living polymer chain end which permits polymerization at higher temperatures and again, reduces the viscosity of the polymer solution allowing for the use of less solvent, and 3) to slow the rate of reaction which permits polymerization at higher temperatures while using the same technology for removing the heat of reaction as had been used in the standard anionic polymerization process. The processing benefits of using Lewis acids to moderate anionic polymerization techniques have been disclosed in U.S. Pat. Nos. 6,391,981; 6,455,651; and 6,492,469, which are herein incorporated by reference. Related information is disclosed in U.S. Pat. Nos. 6,444,767 and 6,686,423, each incorporated herein by reference. The polymer made by such a moderated, anionic polymerization process can have the same structure as one prepared using the conventional anionic polymerization process and as such, this process can be useful in making the polymers of the present invention. For Lewis acid moderated, anionic polymerization processes, reaction temperatures between 100° C. and 150° C. are preferred as at these temperatures it is possible to take advantage of conducting the reaction at very high polymer concentrations. While a stoichiometric excess of the Lewis acid may be used, in most instances there is not sufficient benefit in improved processing to justify the additional cost of the excess Lewis acid. It is preferred to use from about 0.1 to about 1 mole of Lewis acid per mole of living, anionic chain ends to achieve an improvement in process performance with the moderated, anionic polymerization technique.

Preparation of radial (branched) polymers requires a post-polymerization step called "coupling". In the above radial formulas n is an integer of from 2 to about 30, preferably from about 2 to about 15, and more preferably from 2 to 6, and X is the remnant or residue of a coupling agent. A variety of coupling agents are known in the art and can be used in preparing the coupled block copolymers of the present invention. These include, for example, dihaloalkanes, silicon halides, siloxanes, multifunctional epoxides, silica compounds, esters of monohydric alcohols with carboxylic acids, (e.g. methylbenzoate and dimethyl adipate) and epoxidized oils. Star-shaped polymers are prepared with polyalkenyl coupling agents as disclosed in, for example, U.S. Pat. Nos. 3,985,830; 4,391,949; and 4,444,953; as well as Canadian Patent No. 716,645, each incorporated herein by reference. Suitable polyalkenyl coupling agents include divinylbenzene, and preferably m-divinylbenzene. Preferred are tetra-alkoxysilanes such as tetra-methoxysilane (TMOS) and tetra-ethoxysilane (TEOS), tri-alkoxysilanes such as methyltrimethoxysilane (MTMS), aliphatic diesters such as dimethyl adipate and diethyl adipate, and diglycidyl aromatic epoxy compounds such as diglycidyl ethers deriving from the reaction of bis-phenol A and epichlorohydrin.

3. Process to Prepare Hydrogenated Block Copolymers.

As noted, in some cases—i.e., (1) when there is a diene in the B interior blocks, (2) when the A block is a polymer of a 1,3-cyclodiene, (3) when there is an impact modifier block D and (4) when the A block is a polymer of a conjugated diene having a vinyl content of less than 35 mol percent—it is necessary to selectively hydrogenate the block copolymer to remove any ethylenic unsaturation. Hydrogenation generally improves thermal stability, ultraviolet light stability, oxidative stability, and, therefore, weatherability of the final polymer, and reduces any chance for sulfonation of the A block or the D block.

Hydrogenation can be carried out via any of the several hydrogenation or selective hydrogenation processes known in the prior art. For example, such hydrogenation has been accomplished using methods such as those taught in, for example, U.S. Pat. Nos. 3,595,942, 3,634,549, 3,670,054, 3,700,633, and Re. 27,145, the disclosures of which are incorporated herein by reference. These methods operate to hydrogenate polymers containing ethylenic unsaturation and are based upon operation of a suitable catalyst. Such catalyst, or catalyst precursor, preferably comprises a Group VIII metal such as nickel or cobalt which is combined with a suitable reducing agent such as an aluminum alkyl or hydride of a metal selected from Groups I-A, II-A and III-B of the Periodic Table of the Elements, particularly lithium, magnesium or aluminum. This preparation can be accomplished in a suitable solvent or diluent at a temperature from about 20° C. to about 80° C. Other catalysts that are useful include titanium based catalyst systems.

Hydrogenation can be carried out under such conditions that at least about 90 percent of the conjugated diene double bonds have been reduced, and between zero and 10 percent of the arene double bonds have been reduced. Preferred ranges are at least about 95 percent of the conjugated diene double bonds reduced, and more preferably about 98 percent of the conjugated diene double bonds are reduced.

Once the hydrogenation is complete, it is preferable to oxidize and extract the catalyst by stirring with the polymer solution a relatively large amount of aqueous acid (preferably 1 to 30 percent by weight acid), at a volume ratio of about 0.5 parts aqueous acid to 1 part polymer solution. The nature of the acid is not critical. Suitable acids include phosphoric acid, sulfuric acid and organic acids. This stirring is continued at about 50° C. for from about 30 to about 60 minutes while sparging with a mixture of oxygen in nitrogen. Care must be exercised in this step to avoid forming an explosive mixture of oxygen and hydrocarbons.

4. Process to Make Sulfonated Polymers

Once the polymer is polymerized, and if necessary, hydrogenated, it will be sulfonated using a sulfonation agent, by processes known in the art, such as those taught in U.S. Pat. Nos. 3,577,357; 5,239,010 and 5,516,831, each incorporated herein by reference. One process uses acyl sulfates. Acyl sulfates are known in the art as described in "Sulfonation and Related Reactions", E. E. Gilbert, Robert E. Krieger Publishing Co., Inc., Huntington, N.Y., pp 22, 23, and 33 (1977) (First edition published by John Wiley & Sons, Inc. (1965)). The preferred sulfonating reagent is "acetyl sulfate".

The acetyl sulfate route of sulfonation is said to be one of the least harsh and cleanest of the methods. In the acetyl sulfate route, the acetyl sulfate is made by combining concentrated sulfuric acid with a molar excess of acetic anhydride in a suitable solvent such as 1,2-dichloroethane. This is either made prior to the reaction or generated "in situ" in the presence of the polymer. The reported temperature for the sulfonation ranges from 0° C. to 50° C. and the reaction time is typically on the order of 2 to 6 hours. The acetyl sulfate is typically made fresh because it can react with itself over time and at elevated reaction temperatures to form sulfoacetic acid ($HSO_3CH_2COOH$). Sulfonation using acetyl sulfate is often not quantitative, conversion of acetyl sulfate may be 50% to 60% for styrene block copolymer sulfonation although broader ranges may be achieved.

Isolation of sulfonated polymers is often done by steam stripping or by coagulation in boiling water. Once the sulfonation reaction is completed, the block copolymers can be cast directly into an article form (e.g., membrane) without the necessity of isolating the block copolymer as in the previous step. The quantity of molecular units containing sulfonic acid or sulfonate functional groups in the modified block copolymer is dependent on the content and the aromatic structure of the alkenyl arene therein. Once these parameters are fixed, the number of such groups present is dependent on the degree of functionality desired between a minimum and maximum degree of functionality based on these parameters. The minimum degree of functionality corresponds on the average to at least about one (1), preferably at least about three (3) sulfonic acid or sulfonate groups per molecule of the block copolymer. It is presently believed that the addition of about one (1) sulfonic acid or sulfonate group per non-para substituted aromatic group of the B blocks is limiting. Preferably, the functionality is between about 10 and 100% of the non-para substituted aromatic groups in the B blocks, more preferably about 20 to about 90% of such groups, most preferably about 25 to about 75 mol percent.

Another route to sulfonate the polymers is the use of sulfur trioxide as disclosed in U.S. Pat. No. 5,468,574, incorporated herein by reference. Other routes to sulfonate the polymers include (1) reaction with a complex of sulfur trioxide and an ether, and (2) reaction with a triethylphosphate/sulfur trioxide adduct as disclosed in U.S. Pat. No. 5,239,010, incorporated herein by reference. Similar techniques using related phosphorous reagents, include reaction of sulfur trioxide with complexes of phosphorous pentoxide and tris(2-ethylhexyl) phosphate as disclosed in PCT Publication WO 2005/030812 A1; this publication also includes the disclosure of sulfuric acid, preferably using silver sulfate as a catalyst, various chlorosulfonic acid agents, and mixtures of sulfur dioxide with chlorine gas for the sulfonation reaction.

5. Process to Neutralize Sulfonated Polymers

Another embodiment of the present invention is to "neutralize" the modified block copolymer with a base. This may be desirable whenever improved stability of the polymer or enhanced strength of the polymer at elevated temperatures is needed. Neutralization of the sulfonated block copolymer also tends to reduce the corrosive nature of the acid moieties, enhances the driving force for phase separation in the block copolymer, improves resistance to hydrocarbon solvents, and in many instances improves recovery of the sulfonated polymer from the byproducts of the sulfonation reaction.

The sulfonated block copolymer may be at least partly neutralized wherein a portion of the sulfonic functional groups, proton donors or Bronsted acids, have been neutralized with a base, a Bronsted or Lewis Base. Using the definitions of Bronsted and Lewis bases as contained in Chapter 8 and the references therein of Advanced Organic Chemistry, Reactions, Mechanisms, and Structures, Fourth Edition by Jerry March, John Wiley & Sons, New York, 1992, a base is a compound with an available pair of electrons. Optionally, the base could be polymeric or non-polymeric. Illustrative embodiments of the group of non-polymeric bases would include an ionizable metal compound which reacts with the Bronsted acid centers in the sulfonated block copolymer to form metal salts. In one embodiment, the ionizable metal compound comprises a hydroxide, an oxide, an alcoholate, a carboxylate, a formate, an acetate, a methoxide, an ethoxide, a nitrate, a carbonate or a bicarbonate. Preferably the ionizable metal compound is a hydroxide, an acetate, or a methoxide, more preferably the ionizable metal compound is a hydroxide. Regarding the particular metal, it is preferred that the ionizable metal compound comprises $Na+$, $K+$, $Li+$, $Cs+$, $Ag+$, $Hg+$, $Cu+$, $Mg^{2+}$, $Ca^{2+}$, $Sr^{2+}$, $Ba^{2+}$, $Cu^{2+}$, $Cd^{2+}$, $Hg^{2+}$, $Sn^{2+}$, $Pb^{2+}$, $Fe^{2+}$, $Co^{2+}$, $Ni^{2+}$, $Zn^{2+}$, $Al^{3+}$, $Sc^{3+}$, $Fe^{3+}$, $La^{3+}$ or $Y^{3+}$ compounds. Preferably the ionizable metal compound is an $Ca^{2+}$, $Fe^{3+}$, or $Zn^{2+}$ compound, such as zinc acetate, more preferably the ionizable metal compound is a $Ca^{2+}$ compound. Alternatively, amines will react as bases with the acid centers in the sulfonated block copolymers of the present invention to form ammonium ions. Suitable non-polymeric amines would include primary, secondary, and tertiary amines and mixtures thereof wherein the substituents would be linear, branched, or cyclic aliphatic or aromatic moieties or mixtures of the various types of substituents. Aliphatic amines would include ethylamine, diethylamine, triethylamine, trimethylamine, cyclohexylamine, and the like. Suitable aromatic amines would include pyridine, pyrrole, imidazole, and the like. Analogous polymeric amines would include polyethyleneamine, polyvinylamine, polyallylamine, polyvinylpyridene, and the like. With regard to the level of neutralization, it is preferred that the level be between 5 to 100 mol percent of the sulfonation sites, more preferably the level is between 20 and 100 mol percent, even more preferably the level is between 50 to 100 mol percent of the sulfonation sites. Such neutralization is taught in U.S. Pat. Nos. 5,239,010 and 5,516,831, which disclosures are herein incorporated by reference.

Other neutralization techniques include processes wherein a portion of said sulfonic functional groups have been neutralized with aluminum acetylacetonate, such as taught in U.S. Pat. No. 6,653,408, and reaction with an agent represented by the formula $MR_x$, where M is a metal ion, R is selected independently from the group consisting of hydrogen and hydrocarbyl groups and x is an integer from 1 to 4, such as taught in U.S. Pat. No. 5,003,012. The disclosures of U.S. Pat. Nos. 6,653,408 and 5,003,012 are herein incorporated by reference.

In yet another embodiment, the sulfonated block copolymer is modified by a hydrogen bonding interaction with a base, a Bronsted or Lewis Base. Using the definitions of Bronsted and Lewis bases as contained in Chapter 8 and the references therein of Advanced Organic Chemistry, Reactions, Mechanisms, and Structures, Fourth Edition by Jerry March, John Wiley & Sons, New York, 1992, a base is a compound with an available pair of electrons. In this case, the base is not sufficiently strong to neutralize the Bronsted acid centers in the sulfonated block copolymer, but is strong enough to achieve a significant attraction to the sulfonated block copolymer via a hydrogen bonding interaction. As noted above, nitrogen compounds often have an available electron pair and many interact with sulfonic acid centers via hydrogen bonding without effective neutralization of the acid species. Examples of such nitrogen containing materials include nitriles, urethanes, and amides. Their polymeric analogs, polyacrylamide, polyacrylonitrile, nylons, ABS, and polyurethanes, could be used as modifying agents which interact with the sulfonated block copolymer by hydrogen bonding interactions, as well. In a similar way, oxygen containing compounds that have an available pair of electrons that will interact as bases with the acid centers in sulfonated block copolymers forming various oxonium ions. Both polymeric and non-polymeric ethers, esters, and alcohols might be used in this way to modify a sulfonated block copolymer of the present invention. The sulfonated polymers of the present invention may be modified by acid-base hydrogen bonding interactions when combined with glycols, to include polyethylene glycol, and polypropylene glycol, or mixtures of polyethylene glycol and polypropylene glycol alone or with other substituents (i.e., Pluronics® and Pepgel) and the like, polytetrahydrofuran, esters, to include polyethylene terephthalate, polybutyleneterephthalate, aliphatic polyesters, and the like, and alcohols to include polyvinylalcohol, poly saccharides, and starches.

Those of ordinary skill in the art will recognize that in certain instances it might be desirable to further react the sulfonated block copolymer with other substituents such as one or more halogen groups (e.g., fluorine).

With regard to the ionizable metal compounds, it is believed that increased high temperature properties of these ionic copolymers are the result of an ionic attraction between the metal ion and one or more ionized sulfonate functional groups in the B block domain. This ionic attraction results in the formation of ionic crosslinks, which occurs in the solid state. The improvement in the mechanical properties and deformation resistance resulting from the neutralization of the ionic B block domains is greatly influenced by the degree of neutralization and, therefore, the number of the ionic crosslinks and the nature of the crosslink involved. Illustrative embodiments of non-polymeric bases include an ionizable metal compound which reacts to form metal salts. The ionizable metal compound comprises a hydroxide, an oxide, an alcoholate, a carboxylate, a formate, an acetate, a methoxide, an ethoxide, a nitrate, a carbonate or a bicarbonate.

Alternatively, amines can be reacted as bases with the acid centers in the sulfonated block copolymers of the present invention to form ammonium ions. Suitable non-polymeric amines include primary, secondary, and tertiary amines and mixtures thereof wherein the substituents would be linear, branched, or cyclic aliphatic or aromatic moieties or mixtures of the various types of substituents. Aliphatic amines include ethylamine, diethylamine, triethylamine, trimethylamine, cyclohexylamine, and the like. Suitable aromatic amines include pyridine, pyrrole, imidazole, and the like. Analogous polymeric amines would include polyethyleneamine, polyvinylamine, polyallylamine, polyvinylpyridene, and the like.

Examples of nitrogen containing materials include nitriles, urethanes, and amides, and their polymeric analogs, polyacrylamide, polyacrylonitrile, nylons, ABS, and polyurethanes. Suitable examples of oxygen containing compounds include both polymeric and non-polymeric ethers, esters, and alcohols.

The degree of sulfonation and of neutralization may be measured by several techniques. For example, infrared analysis or elemental analysis may be employed to determine the overall degree of functionality. Additionally, the titration of a solution of the block copolymer with a strong base may be utilized to determine the degree of functionality and/or the degree of neutralization (metal sulfonate salt content). Neutralization as used herein is based on the percentage of sulfonate ions as compared to the total sulfonic acid and sulfonate group functionality. Reaction conditions and processes are disclosed further in the examples and in U.S. Pat. Nos. 5,239,010 and 5,516,831, the disclosures of which are herein incorporated by reference.

6. Isolation of Sulfonated Polymers

In one embodiment, the last step, following all polymerization(s) and sulfonation reactions as well as any desired post-treatment processes, is a finishing treatment to remove the final polymer from the solvent. Various means and methods are known to those skilled in the art, and include use of steam to evaporate the solvent, and coagulation of the polymer followed by filtration. Coagulation with a non-solvent followed by filtration has been used to isolate the sulfonated polymers, as well. In instances where the spent reagents and byproducts are volatile, recovery in a fluidized bed drier could be used. Following any one of these finishing treatments in this embodiment, it is preferable to wash the resulting polymer one or more times in water in order to remove any reagent residues that remain from the sulfonation process. When water is added to the resulting polymer, a solid-in-liquid suspension having a milky white color is obtained. The polymer is removed from the opaque suspension by either filtering the final product out of the suspension or allowing the polymer to settle and then removing the aqueous phase. In an alternative embodiment, once the sulfonation reaction is completed, the block copolymers are cast directly into an article form (e.g., membrane) without the necessity of isolating the block copolymer as in the previous step. In this particular embodiment the article (e.g., membrane) can be submerged in water and will retain its form (solid) while in the water. In other words, the block copolymer will not dissolve in water or disperse in water.

Independent of the method of isolation, the final result is a "clean" block copolymer useful for a wide variety of challenging applications, according to the properties thereof.

7. Properties of Sulfonated Polymers

The polymers of the present invention, as a direct consequence of being selectively sulfonated in the interior segment of one of the block copolymers mentioned above, e.g., an interior segment of a saturated triblock copolymer, have a unique balance of physical properties, which render them extraordinarily useful in a variety of applications. As the inventive sulfonated block copolymers are not crosslinked, these copolymers may be cast into membranes or coatings. In the casting process, the copolymers tend to self assemble into microphase separated structures. The sulfonate groups organize into a separate phase or ion channels. When these channels form a continuous structure spanning the distance between the two sides of the membrane they have a remarkable ability to transport water and protons.

It is the integrity of the phase formed as a consequence of the separation of the end segments, which provides the membrane with strength. As the end segments have little or no sulfonate functionality, they are extremely resistant to being plasticized by the addition of water, as well as by methanol. It is this effect that allows the generation of membranes with good wet strength. The hardness and flexibility of the membrane can be easily adjusted in two ways. The styrene content of the interior segment (B block) of the precursor block copolymer can be increased from a low level to 100% wt. As the styrene content of the interior segment is increased, the product sulfonated block copolymer membrane will become harder and less flexible. Alternatively, the end segment (A block) content of the precursor block copolymer may be increased from about 10% wt to about 90% wt with the effect that the resulting sulfonated block copolymer membrane will become harder and less flexible as the end block content of the polymer is increased. At lower end block contents, the membrane will be too weak; at end block contents above about 90% wt, the product membranes will have poor transport properties.

By adjusting the structure of the precursor block copolymer, sulfonated polymer membranes may be prepared having surprising wet strength, well controlled and high rates of water and/or proton transport across the membrane, exceptional barrier properties for organic and non-polar liquids and gases, tunable flexibility and elasticity, controlled modulus, and oxidative and thermal stability. It is expected that the membranes would have good resistance to methanol transport and good retention of properties in the presence of methanol. As these membranes are not crosslinked, they can be reshaped or reprocessed by redissolving them in solvent and recasting the resulting solution; they may be reused or reshaped using various polymer melt processes, also.

An interesting feature of these uniformly microphase separated materials is that one phase readily absorbs water while the second phase is a much less polar thermoplastic. Water in the sulfonated phase could be heated using any of a variety of indirect methods, exposure to microwave or radio frequency radiation, to name a couple; the water heated in this way might transfer sufficient heat to the thermoplastic phase to allow softening or flow in this phase. Such a mechanism could be the basis for polymer "welding" or molding operations that would not require direct heating of the thermoplastic phase. Such a process could be very efficient because it doesn't require heating the whole part, fast because intensity can be controlled over a wide range, and safe because only the irradiated area will be hot resulting in lower overall part temperature. Such a process would be well suited to the assembly of articles from pieces of fabric. Rather than stitching the pieces together, they might be "welded" together—no stitching holes. It might also be used for electronic assemblies and building construction. In a related concept, films (to include compounded adhesive films) prepared from polymers of the present invention could be applied as single use adhesives and subsequently removed by treatment with water.

As shown in the examples that follow, the block copolymers of the present invention have a number of significant and unexpected properties. For example, sulfonated block copolymers according to the present invention have a water permeability greater than 0.1 times 10-6, preferably greater than 1.0 times 10-6, grams per Pascal.meter.hour according to ASTM E96-00 "desiccant" method, a wet tensile strength greater than 100 psi, preferably greater than 500 psi, according to ASTM D412, and a swellability of less than 100% by weight. In contrast, as shown in the examples, at sulfonation levels (presence of —SO3H units) above about 1.5 mmol/g polymer, the polymers of the prior art have little, if any, wet tensile strength. Whereas, the polymers of the present invention typically have wet tensile strengths above 500 psi, and in many cases about 1000 psi. Further, it has been shown that polymers of the present invention have a ratio of wet tensile strength to dry tensile strength greater than 0.3.

8. End Uses, Compounds and Applications

The sulfonated block copolymers according to the present invention can be used in a variety of applications and end uses. Such polymers having selectively sulfonated interior blocks will find utility in applications where the combination of good wet strength, good water and proton transport characteristics, good methanol resistance, easy film or membrane formation, barrier properties, control of flexibility and elasticity, adjustable hardness, and thermal/oxidative stability are important. In one embodiment of the present invention, the inventive sulfonated block copolymers are used in electrochemical applications, such as in fuel cells (separator phase), proton exchange membranes for fuel cells, dispersions of metal impregnated carbon particles in sulfonated polymer cement for use in electrode assemblies, including those for fuel cells, water electrolyzers (electrolyte), acid batteries (electrolyte separator), super capacitors (electrolyte), separation cell (electrolyte barrier) for metal recovery processes, sensors (particularly for sensing humidity) and the like. The inventive sulfonated block copolymers are also used as desalination membranes, coatings on porous membranes, absorbents, personal hygiene articles, water gels and as adhesives. Additionally, the inventive block copolymers are used in protective clothing and breathable fabric applications where the membranes, coated fabrics, and fabric laminates could provide a barrier of protection from various environmental elements (wind, rain, snow, chemical agents, biological agents) while offering a level of comfort as a result of their ability to rapidly transfer water from one side of the membrane or fabric to the other, e.g., allowing moisture from perspiration to escape from the surface of the skin of the wearer to the outside of the membrane or fabric and vice versa. Full enclosure suits made from such membranes and fabrics might protect first responders at the scene of an emergency where exposure to smoke, a chemical spill, or various chemical or biological agents are a possibility. Similar needs arise in medical applications, particularly surgery, where exposure to biological hazards is a risk. Surgical gloves and drapes fabricated from these types of membranes are other applications that could be useful in a medical environment. Articles fabricated from these types of membranes could have antibacterial and/or antiviral and/or antimicrobial properties as reported in U.S. Pat. Nos. 6,537,538, 6,239,182, 6,028,115, 6,932,619 and 5,925,621 where it is noted that polystyrene sulfonates act as inhibitory agents against HIV (human immunodeficiency virus) and HSV (herpes simplex virus. In personal hygiene applications, a membrane or fabric of the present invention that would transport water vapor from perspiration while providing a barrier to the escape of other bodily fluids and still retain its strength properties in the wet environment would be advantageous. The use of these types of materials in diapers and adult incontinence constructions would be improvements over existing technologies.

Fabrics can be made by either solution casting the sulfonated polymer on a liner fabric, or laminating a film of the sulfonated polymer between a liner fabric and a shell fabric.

The sulfonated block copolymers of the present invention can also be used in absorbent articles, and in particular with super absorbent materials. In particular, the sulfonated block copolymers could be used to contain and/or distribute water to the super absorbent particles. For example, the super absorbent particles could be encased in a film of the sulfonated block copolymer. In other embodiments, the materials of the present invention will be resistant to bacterial build up. The use of water-swellable, generally water-insoluble absorbent materials, commonly known as super absorbents, in disposable absorbent personal care products is known. Such absorbent materials are generally employed in absorbent products such as, for example, diapers, training pants, adult incontinence products, and feminine care products in order to increase the absorbent capacity of such products, while reducing their overall bulk. Such absorbent materials are generally present as a composite of super absorbent particles (SAP) mixed in a fibrous matrix, such as a matrix of wood pulp fluff. A matrix of wood pulp fluff generally has an absorbent capacity of about 6 grams of liquid per gram of fluff The super absorbent materials (SAM) generally have an absorbent capacity of at least about 10 grams of liquid per gram of SAM, desirably of at least about 20 grams of liquid per gram of SAM, and often up to about 40 grams of liquid per gram of SAM.

In one embodiment of the present invention, the super absorbent material comprises a sodium salt of a cross-linked polyacrylic acid. Suitable super absorbent materials include, but are not limited to: Dow AFA-177-140 and Drytech 2035 both available from Dow Chemical Company, Midland, Mich.; Favor SXM-880 available from Stockhausen, Inc. of Greensboro, N.C.; Sanwet IM-632 available from Tomen America of New York, N.Y.; and Hysorb P-7050 available from BASF Corporation, Portsmouth, Va. Desirably, the absorbent composites of the present invention contain the above-described super absorbent materials in combination with the sulfonated block copolymers of the present invention, optionally containing a fibrous matrix containing one or more types of fibrous materials.

Applications such as coatings for potable water transport and storage devices would take advantage of the combination of good mechanical properties of these polymers in wet environments with their tendency to resist the growth of biologically active species. This feature of block copolymers selectively sulfonated in the interior segment might be usefully applied to waste water (both sewage and industrial waste) pipe and treatment facilities. In a like manner, polymers of the present invention might be used to inhibit mold growth on the surfaces of building materials. These polymers may well inhibit the growth of larger organisms as would be useful in avoiding fouling in various marine applications. It is known to use the self-assembly feature of selectively sulfonated block copolymers for the construction of humidity exchange cells as described in U.S. Pat. No. 6,841,601. In this application, polymers of the present invention would allow the fabrication of membrane elements with good wet strength and would not require reinforcement. This could simplify the construction of membrane energy recovery devices. Nonwoven house wrap material, such as TYVEK® supplied by DuPont, are currently used in home construction to keep the elements of wind and weather from penetrating the exterior of the house. In some environments, this technology does not allow sufficient transport of water vapor through the walls of the house with the result that conditions for the growth of mold develop in the walls of the home. An assembly prepared from polymers of the present invention might provide equally good barrier performance with the advantage of allowing effective escape of water vapor from the walls of the house. In a similar way, there is a need for a backing material for carpets that allows the transport for water vapor. This need is critical in homes that use concrete slab construction where water flow through the concrete can be significant in periods of high humidity or excessive rain. If the carpet backing does not transport the water vapor at an equal rate, the build up of condensed water between the back of carpet and the surface of the slab can be problematic. Carpets backed with a polymer coating based upon polymers of the present invention could overcome this problem.

The sulfonated polymers of the present invention may also be used as flame retardant materials—particularly for spraying a flammable article in the path of an advancing fire. Such sulfonated polymers may be an excellent "carrier" for conventional ignition retardant materials, which tend not to be compatible with conventional hydrocarbon polymers.

Furthermore, the inventive sulfonated block copolymers can also be used as a membrane to gather moisture from the environment. Accordingly, such membranes may be used to collect fresh water from the atmosphere in a situation where there is no ready supply of decent quality water.

Further, the copolymers of the present invention can be compounded with other components not adversely affecting the copolymer properties. The block copolymers of the present invention may be blended with a large variety of other polymers, including olefin polymers, styrene polymers, tackifying resins, hydrophilic polymers and engineering thermoplastic resins, with polymer liquids such ionic liquids, natural oils, fragrances, and with fillers such as nanoclays, carbon nanotubes, fullerenes, and traditional fillers such as talcs, silica and the like.

In addition, the sulfonated polymers of the present invention may be blended with conventional styrene/diene and hydrogenated styrene/diene block copolymers, such as the styrene block copolymers available from Kraton Polymers LLC. These styrene block copolymers include linear S-B-S, S-I-S, S-EB-S, S-EP-S block copolymers. Also included are radial block copolymers based on styrene along with isoprene and/or butadiene and selectively hydrogenated radial block copolymers.

Olefin polymers include, for example, ethylene homopolymers, ethylene/alpha-olefin copolymers, propylene homopolymers, propylene/alpha-olefin copolymers, high impact polypropylene, butylene homopolymers, butylene/alpha olefin copolymers, and other alpha olefin copolymers or interpolymers. Representative polyolefins include, for example, but are not limited to, substantially linear ethylene polymers, homogeneously branched linear ethylene polymers, heterogeneously branched linear ethylene polymers, including linear low density polyethylene (LLDPE), ultra or very low density polyethylene (ULDPE or VLDPE), medium density polyethylene (MDPE), high density polyethylene (HDPE) and high pressure low density polyethylene (LDPE). Other polymers included hereunder are ethylene/acrylic acid (EEA) copolymers, ethylene/methacrylic acid (EMAA) ionomers, ethylene/vinyl acetate (EVA) copolymers, ethylene/vinyl alcohol (EVOH) copolymers, ethylene/cyclic olefin copolymers, polypropylene homopolymers and copolymers, propylene/styrene copolymers, ethylene/propylene copolymers, polybutylene, ethylene carbon monoxide interpolymers (for example, ethylene/carbon monoxide (ECO) copolymer, ethylene/acrylic acid/carbon monoxide terpolymer and the like). Still other polymers included hereunder are polyvinyl chloride (PVC) and blends of PVC with other materials.

Styrene polymers include, for example, crystal polystyrene, high impact polystyrene, medium impact polystyrene, styrene/acrylonitrile copolymers, styrene/acrylonitrile/butadiene (ABS) polymers, syndiotactic polystyrene, sulfonated polystyrene and styrene/olefin copolymers. Representative styrene/olefin copolymers are substantially random ethylene/ styrene copolymers, preferably containing at least 20, more preferably equal to or greater than 25 weight percent copolymerized styrene monomer.

For the purposes of the specification and claims, the term "engineering thermoplastic resin" encompasses the various polymers such as for example thermoplastic polyester, thermoplastic polyurethane, poly(aryl ether) and poly(aryl sulfone), polycarbonate, acetal resin, polyamide, halogenated thermoplastic, nitrile barrier resin, poly(methyl methacrylate) and cyclic olefin copolymers, and further defined in U.S. Pat. No. 4,107,131, the disclosure of which is hereby incorporated by reference.

Tackifying resins include polystyrene block compatible resins and midblock compatible resins. The polystyrene block compatible resin may be selected from the group of coumarone-indene resin, polyindene resin, poly(methyl indene) resin, polystyrene resin, vinyltoluene-alphamethylstyrene resin, alphamethylstyrene resin and polyphenylene ether, in particular poly(2,6-dimethyl-1,4-phenylene ether). Such resins are e.g. sold under the trademarks "HERCURES", "ENDEX", "KRISTALEX", "NEVCHEM" and "PICCOTEX". Resins compatible with the hydrogenated (interior) block may be selected from the group consisting of compatible C5 hydrocarbon resins, hydrogenated C5 hydrocarbon resins, styrenated C5 resins, C5/C9 resins, styrenated terpene resins, fully hydrogenated or partially hydrogenated C9 hydrocarbon resins, rosins esters, rosins derivatives and mixtures thereof. These resins are e.g. sold under the trademarks "REGALITE", "REGALREZ", "ESCOREZ" and "ARKON.

Hydrophilic polymers include polymeric bases which are characterized as having an available pair of electrons. Examples of such bases include polymeric amines such as polyethyleneamine, polyvinylamine, polyallylamine, polyvinylpyridene, and the like; polymeric analogs of nitrogen containing materials such as polyacrylamide, polyacrylonitrile, nylons, ABS, polyurethanes and the like; polymeric analogs of oxygen containing compounds such as polymeric ethers, esters, and alcohols; and acid-base hydrogen bonding interactions when combined with glycols such as polyethylene glycol, and polypropylene glycol, and the like, polytetrahydrofuran, esters (including polyethylene terephthalate, polybutyleneterephthalate, aliphatic polyesters, and the like), and alcohols (including polyvinylalcohol), poly saccharides, and starches. Other hydrophilic polymers that may be utilized include sulfonated polystyrene. Hydrophilic liquids such as ionic liquids may be combined with the polymers of the present invention to form swollen conductive films or gels. Ionic liquids such as those described in U.S. Pat. Nos. 5,827,602 and 6,531,241 (which disclosures are herein incorporated by reference) could be introduced into the sulfonated polymers either by swelling a previously cast membrane, or by adding to the solvent system before casting a membrane, film coating or fiber. Such a combination might find usefulness as a solid electrolyte or water permeable membrane.

Exemplary materials that could be used as additional components would include, without limitation:
1) pigments, antioxidants, stabilizers, surfactants, waxes, and flow promoters;
2) particulates, fillers and oils; and
3) solvents and other materials added to enhance processability and handling of the composition.

With regard to the pigments, antioxidants, stabilizers, surfactants, waxes and flow promoters, these components, when utilized in compositions with the sulfonated block copolymers of the present invention may be included in amounts up to and including 10%, i.e., from 0 to 10%, based on the total weight of the composition. When any one or more of these components are present, they may be present in an amount from about 0.001 to about 5%, and even more preferably from about 0.001 to about 1%.

With regard to particulates, fillers and oils, such components may be present in an amount up to and including 50%, from 0 to 50%, based on the total weight of the composition. When any one or more of these components are present, they may be present in an amount from about 5 to about 50%, preferably from about 7 to about 50%.

Those of ordinary skill in the art will recognize that the amount of solvents and other materials added to enhance processability and handling of the composition will in many cases depend upon the particular composition formulated as well as the solvent and/or other material added. Typically such amount will not exceed 50%, based on the total weight of the composition.

The sulfonated block copolymers of the present invention can be used to make any of the articles noted above and in many instances will take any number of forms such as in the form of a film, sheet, coating, band, strip, profile, molding, foam, tape, fabric, thread, filament, ribbon, fiber, plurality of fibers or, fibrous web. Such articles can be formed by a variety of processes such as for example casting, injection molding, over molding, dipping, extrusion (when the block copolymer is in neutralized form), roto molding, slush molding, fiber spinning (such as electrospinning when the block copolymer is in neutralized form), film making, painting or foaming Applicants further claim a method of varying the transport properties of a film cast out of the block copolymers of the present invention. By using a solvent mixture that comprises two or more solvents selected from polar solvents and non-polar solvents, it is possible to obtain different structures which demonstrate different mechanisms of storing water. This in turn allows for the use of the block copolymers of the present invention to fine tune transport properties for particular uses utilizing a single class of block copolymers, i.e., the block copolymers of the present invention. Preferably, the polar solvents utilized in the method of the present invention are selected from water, alcohols having from 1 to 20 carbon atoms, preferably from 1 to 8 carbon atoms, more preferably from 1 to 4 carbon atoms; ethers having from 1 to 20 carbon atoms, preferably from 1 to 8 carbon atoms, more preferably from 1 to 4 carbon atoms, including cyclic ethers; esters of carboxylic acids, esters of sulfuric acid, amides, carboxylic acids, anhydrides, sulfoxides, nitriles, and ketones having from 1 to 20 carbon atoms, preferably from 1 to 8 carbon atoms, more preferably from 1 to 4 carbon atoms, including cyclic ketones. More specifically, the polar solvents are selected from methanol, ethanol, propanol, isopropanol, dimethyl ether, diethyl ether, dipropyl ether, dibutyl ether, substituted and unsubstituted furans, oxetane, dimethyl ketone, diethyl ketone, methyl ethyl ketone, substituted and unsubstituted tetrahydrofuran, methyl acetate, ethyl acetate, propyl acetate, methylsulfate, dimethylsulfate, carbon disulfide, formic acid, acetic acid, sulfoacetic acid, acetic anhydride, acetone, cresol, creosol, dimethylsulfoxide (DMSO), cyclohexanone, dimethyl acetamide, dimethyl formamide, acetonitrile, water and dioxane, with water, tetrahydrofuran, methanol, ethanol, acetic acid, sulfoacetic acid, methylsulfate, dimethylsulfate, and IPA being the more preferred of the polar solvents.

Preferably the non-polar solvents utilized in the method of the present invention are selected from toluene, benzene, xylene, mesitylene, hexanes, heptanes, octanes, cyclohexane, chloroform, dichloroethane, dichloromethane, carbon tetrachloride, triethylbenzene, methylcyclohexane, isopentane, and cyclopentane, with toluene, cyclohexane, methylcyclohexane, cyclopentane, hexanes, heptanes, isopentane, and dichloroethane being the most preferred non-polar solvents. As noted, the method utilizes two or more solvents.

This means that two, three, four or more solvents selected from polar solvents alone, non-polar solvents alone or a combination of polar solvents and non-polar solvents may be used. The ratio of the solvents to one another can vary widely. For examples, in solvent mixtures having two solvents, the ratio can range from 99.99: 0.01 to 0.01:99.9. The conditions under which the films are cast can vary. Preferably, the films will be cast in air, at a temperature from 10° C. to 200° C., preferably room temperature and onto the surface from which the film can be released easily. Alternately the cast solution may be contacted with a non-solvent for the polymer, thereby removing the solvent and forming the solid film or article. Alternately a coated fabric may be prepared by passing the woven or non-woven fabric through a solution of the polymer. The solvent can then be removed by drying or by extraction using a non-solvent for the polymer.

The following examples are intended to be illustrative only, and are not intended to be, nor should they be construed as limiting in any way of the scope of the present invention Illustrative Embodiment #1

As polystyrene is selectively sulfonated in the para position, the inventors surmised that a polystyrene which had an alkyl group blocking the para position would be less susceptible to sulfonation; it would tend to be slower to sulfonate or even completely resistant to sulfonation. In order to test this hypothesis, an experiment was conducted on a 50/50 (w/w) mixture of polystyrene (48,200 Mn) and poly(para-tert-butylstyrene) of about 22,000 Mn. The mixture was sulfonated, targeting 30 mol % of the polystyrene segments for sulfonation. The whole sulfonation reaction mixture was directly passed through alumina twice in order to remove the sulfonated polymeric material. The unabsorbed polymer solution was then dried and the resultant beige colored polymer was extracted with methanol to remove sulfonating reagents. The polymer was dried again under vacuum. The sulfonated, unabsorbed mixture and the original unreacted mixture were analyzed by quantitative 13C NMR and 1H NMR to determine the amount of styrene and para-tert-butylstyrene present (Table 1).

TABLE 1

NMR analysis of eluate for unreacted polymer.

| Polymer Sample Preparation | Polystyrene Content (wt %) | Poly-p-t-butylstyrene (wt %) | Method of Analysis |
|---|---|---|---|
| 50/50 mix before sulfonation | 49.3 | 50.7 | $^1$H NMR |
| 50/50 mix after sulfonation and chromatography | 6.2 | 93.8 | $^1$H NMR |
| 50/50 mix after sulfonation and chromatography | 7.0 | 93.0 | $^{13}$C NMR |

Clearly, the sulfonation reaction favors the polystyrene residues over the poly-para-tert-butylstyrene residues. Accordingly, polymer blocks of para-tert-butyl styrene are resistant to sulfonation and polymer blocks of unsubstituted styrene are susceptible to sulfonation.

Illustrative Embodiment #2

In this example, we have characterized various polymers prior to sulfonation. The block copolymers used in the sulfonation examples are described below in Table #2.

TABLE 2

| | Base Polymers | | | | |
|---|---|---|---|---|---|
| Polymer ID | Polymer Type | Total PSC (% wt) | Interior block PSC (% wt) | ptBS Content (% wt) | Apparent $MW_s$ 2-arm (kg/mol) | $M_n$ (true) 2-arm (kg/mol) |
| COMPARATIVE EXAMPLES | | | | | | |
| Aldrich-1 | S-E/B-S | 29 | 0 | 0 | 106 | 71 |
| G-1 | S-E/B-S | 30 | 0 | 0 | 80 | 54 |
| G-2 | S-E/B-S | 30 | 0 | 0 | 112 | 71 |
| A-1 | S-S/E/B-S | 38 | 25 | 0 | 147 | 105 |
| A-2 | S-S/E/B-S | 66 | 50 | 0 | 233 | 197 |
| A-3 | S-S/E/B-S | 64 | 49 | 0 | 136 | 107 |
| INVENTIVE EXAMPLES | | | | | | |
| T-1 | (ptBS-S/E/B)$_n$ | 31 | 50 | 42 | 167 | 188 |
| T-2 | (ptBS-S/E/B)$_n$ | 40 | 50 | 22 | 132 | 126 |
| T-2.1 | (ptBS-S/E/B)$_n$ | 22 | 36 | 47 | 102 | 100 |
| T-3 | (ptBS/S-S/E/B)$_n$ | 42 | 50 | 22 | 145 | 137 |
| T-4 | (ptBS-S)$_n$ | 67 | 100 | 33 | 142 | 170 |
| T-5 | (ptBS-S)$_n$ | 68 | 100 | 32 | 174 | 212 |
| P-1 | (pMS-S)$_n$ | 67 | 100 | 0 | 124 | 132 |
| E-1 | (PE-S)$_n$ | 67 | 100 | 0 | 180 | 153 |
| TS-1 | (ptBS-E/B-S)$_n$ | 34 | 63 | 34 | 96 | 85 |
| TS-2 | (ptBS-E/B-S)$_n$ | 42 | 73 | 43 | 67 | 75 |

TABLE 2-continued

Base Polymers

| Polymer ID | Polymer Type | Total PSC (% wt) | Interior block PSC (% wt) | ptBS Content (% wt) | Apparent $MW_s$ 2-arm (kg/mol) | $M_n$ (true) 2-arm (kg/mol) |
|---|---|---|---|---|---|---|
| TS-3 | (ptBS-E/B-S)$_n$ | 35 | 60 | 36 | 91 | 79 |
| TS-4 | (ptBS-E/B-S)$_n$ | 41 | 70 | 45 | 61 | 68 |

Where S = styrene, E = ethylene, B = butylene, ptBS = para-tert-butylstyrene, E/B is hydrogenated polybutadiene, pMS = p-methylstyrene and PE = hydrogenated low vinyl content (around 10% 1,2-addition) polybutadiene, for (ptBS-E/B-S)x polymers E/B-S was considered the interior block for the purpose of calculating the "Interior block PSC (%), "Apparent MWs 2-arm (kg/mol)" is the molecular weight of the linear triblock component (2-arm for coupled polymers) of the product mixture as measured by GPC (calibrated with polystyrene), "Mn(true) 2-arm (kg/mol)" is the Apparent MW value which has been adjusted to estimate the actual MW of the triblock copolymer using the following factors (adjusted based upon the MW of the monomer) to adjust the polystyrene equivalent molecular weight to true MW values: for polystyrene, multiply the apparent MW by wt % polystyrene times 1.0, for hydrogenated polybutadiene (E/B), multiply the apparent MW by % wt hydrogenated polybutadiene times 0.54, for ptBS, multiply the apparent MW by wt % poly-para-tert-butylstyrene times 1.6, and for pMS, multiply the apparent MW by % wt para-methylstyrene times 1.2. "Aldrich-1" was used as purchased from Aldrich Chemical Company (Product number 448885).

The information provided with the Aldrich-1 sample indicated that it was a sulfonated, selectively hydrogenated S-B-S triblock copolymer. The polymers noted G-1 and G-2 are selectively hydrogenated, S-B-S, triblock copolymers available from KRATON Polymers. Polymers labeled A-1, A-2 and A-3 are selectively hydrogenated ABA triblock copolymers where the A blocks are styrene polymer blocks and the B block prior to hydrogenation is a controlled distribution block copolymer of styrene and butadiene, manufactured according to the process disclosed in U.S. Published Patent Application No. 2003/0176582. Hydrogenation using the procedure described in the above noted Published Patent Application afforded Polymers A-1, A-2 and A-3.

Polymers labeled T-1, T-2 and T-2.1 are selectively hydrogenated (A-B)nX block copolymers where the A block is a polymer block of para-tert-butylstyrene which was found to be resistant to sulfonation and the B block is an hydrogenated controlled distribution block of butadiene and styrene which was found to be susceptible to sulfonation. These three polymers were prepared using essentially the same process but slightly different quantities of the various monomers. The A block was prepared by anionic polymerization of p-t-butyl-styrene (ptBS) in cyclohexane (about 40° C.) using s-BuLi as the initiator. The living poly-p-t-butylstyrene in cyclohexane solution was combined with the distribution control agent (diethyl ether (DEE), 6%wt). Using the procedure described in U.S. Published Patent Application No. 2003/0176582, a controlled distribution of styrene in butadiene polymer segment was polymerized onto the poly-p-t-butylstyrene end segment. The resulting diblock copolymer was coupled using methyl trimethoxysilane (Si/Li=0.45/1 (mol/mol)). The coupled polymer was a mostly linear A-B-A triblock copolymer. Hydrogenation using a standard Co2+/triethylaluminum method afforded the polymers described in Table 2.

The polymer labeled T-3 is similar to T-2, except that the A block is a random copolymer block of unsubstituted styrene and p-t-butyl styrene. This polymer was prepared by a similar process with the exception that a mixture of p-t-butylstyrene and styrene (90/10 (wt/wt)) was used in the anionic polymerization of the A block copolymer. The remainder of the synthesis was as described for the preparation of T-2. Again a mostly linear polymer triblock copolymer was obtained. As over 97% of the unsubstituted styrene monomer was in the B block of the copolymer, the A blocks were resistant to sulfonation and the B blocks were sulfonation susceptible.

The polymers labeled T-4 and T-5 are unhydrogenated block copolymers (A-B)nX where the A block is a polymer block of para-tert-butyl styrene and the B block is a polymer block of unsubstituted styrene. In the preparation of T-4 and T-5, anionic polymerization of p-t-butylstyrene in cyclohexane was initiated using s-BuLi affording an A block having an estimated molecular weight of about 26,000 g/mol. The solution of living poly-p-t-butylstyrene in cyclohexane was treated with styrene monomer. The ensuing polymerization gave a living diblock copolymer having a B block composed only of polystyrene. The living polymer solution was coupled using tetramethoxysilane (Si/Li=0.40/1 (mol/mol)). A mixture of branched (major component) and linear coupled polymers was obtained. As the interior segments of these polymers contained only polystyrene and the end segments contained only poly-p-t-butylstyrene, the interior segments of these polymers were much more susceptible to sulfonation than were the end segments.

The polymer labeled P-1 is an unhydrogenated block copolymer (A-B)nX block copolymer where the A block is a polymer block of para-methylstyrene and the B block is a polymer block of unsubstituted styrene. In the preparation of P-1, anionic polymerization of p-methylstyrene (used as received from Deltech) in cyclohexane was initiated using s-BuLi. Polymerization was controlled over the temperature range of 30° C. to 65° C. affording an A block having a MW (styrene equivalent) of 20,100. The solution of living poly-p-methylstyrene in cyclohexane was treated with styrene monomer (50° C.). The ensuing polymerization gave a living diblock copolymer (styrene equivalent MW=60,200) having a B block composed only of polystyrene. The living polymer solution was coupled using tetramethoxysilane (Si/Li=0.53/1 (mol/mol)). A mixture of branched (minor component) and linear coupled polymers was obtained. As the interior segments of these polymers contained only polystyrene and the end segments contained only poly-p-methylstyrene, one would expect that the interior segments of these polymers would be much more susceptible to sulfonation than were the end segments.

The polymer labeled E-1 is a selectively hydrogenated (A-B)nX block copolymer where the A block is a semi crystalline, polyethylene-like block of hydrogenated, low in vinyl content, polybutadiene which was found to be resistant to sulfonation and the B block is polystyrene which was found to be susceptible to sulfonation. The A block was prepared by anionic polymerization of 1,3-butadiene in cyclohexane over a temperature range from 30° C. to 60° C. using s-BuLi as the initiator. The polymerization took a little over an hour to go to completion. An aliquot of the living polymer solution was quenched by the addition of MeOH and analyzed using a H-NMR technique. Only 9% of the butadiene had polymerized by 1,2-addition (vinyl addition). The living, low in vinyl content, polybutadiene in cyclohexane solution was reacted with styrene (50° C., about half an hour) to prepare the B block. The resulting, living diblock copolymer was coupled using tetramethoxysilane (Si/Li=0.52/1 (mol/mol)). The coupling reaction was allowed to proceed overnight at 70° C. The coupled polymer was a mostly linear A-B-A triblock copolymer. Hydrogenation (70° C., 650 psig, about 2 hr) using a standard Co2+/triethylaluminum (30 ppm Co) method afforded the polymer described in Table 2. An aliquot of the polymer solution was dried to remove the solvent. The dry polymer was easily compression molded at 200° C. (well above the melting point of the semi-crystalline A blocks) into a thin film; this was a demonstration of the thermoplastic nature of the block copolymer.

The polymer labeled TS-1 is a selectively hydrogenated (A-D-B)nX block copolymer where the A block is a polymer block of para-tert-butyl styrene and the B block is a polymer block of unsubstituted styrene. The block labeled D is hydrogenated butadiene and X is a silicon containing residue of the coupling agent. In the preparation of TS-1, anionic polymerization of p-t-butylstyrene in cyclohexane was initiated using s-BuLi affording an A block having an estimated molecular weight of about 22,000 g/mol. Diethyl ether (6%wt of the total solution) was added to the solution of living poly-p-t-butylstyrene (ptBS-Li) in cyclohexane. The ether-modified solution was treated with sufficient butadiene to afford a second segment with a molecular weight of 28,000 g/mol (ptBS-Bd-Li). The polybutadiene segment had a 1,2-addition content of 40% wt. The living (ptBS-Bd-Li) diblock copolymer solution was treated with styrene monomer. The ensuing polymerization gave a living triblock copolymer (ptBS-Bd-S—Li) having a third block composed only of polystyrene (S block MW=25,000 g/mol). The living polymer solution was coupled using tetramethoxysilane (Si/Li=0.41/1 (mol/mol)). A mixture of branched, ((ptBS-Bd-S)3) (major component) and linear ((ptBS-Bd-S)2) coupled polymers was obtained. Hydrogenation using the method described above for T-1 and T-2 removed the C=C unsaturation in the butadiene portion of the pentablock copolymer affording the desired (A-D-B) nX block copolymer. As the interior segment of this polymers contained only polystyrene and the end segments contained only poly-p-t-butylstyrene, the interior segments of these polymers were much more susceptible to sulfonation than were the end segments. The hydrogenated Bd segment, an E/B copolymer, was sulfonation resistant and acted as a toughening spacer block between the poly-p-t-butylstyrene end segments and the sulfonated polystyrene center segment. Polymers TS-2, TS-3, and TS-4 were prepared using the methods described above for the preparation of polymer TS-1 but used differing amounts of the monomers to afford the materials described in Table 2.

Illustrative Embodiment #3

The polymers described in Illustrative Embodiment #2 were sulfonated according to the procedure of the present invention.

In a representative experiment, an elastomeric triblock copolymer, polymer labeled T-2 from Table 2, having sulfonation resistant end segments and a sulfonation susceptible interior segment was treated with acetylsulfate, a sulfonation agent. The triblock copolymer having poly-t-butylstyrene (ptBS) end segments and a interior segment synthesized by selective hydrogenation of a butadiene (Bd) and styrene (S) copolymer (S/E/B) having a controlled distribution of the two monomers, ptBS-S/E/B-ptBS (20 g), was dissolved in 1,2-dichloroethane (DCE) (400m1) and the solution heated to 43 C. The acetylsulfate reagent was prepared in a separate vessel by combining a cold (ice bath) solution of acetic anhydride (AcOAc) (10.85 g, 0.106 mol) in DCE (40 ml) with cold sulfuric acid (6.52 g, 0.067 mol). The cold solution of acetylsulfate was added with stirring to the polymer in DCE. Sulfonation conditions were maintained for 4.5 hr. The triblock copolymer, which had been selectively sulfonated in the interior segment, was isolated from boiling water, washed with an excess of water (until the wash water was neutral in pH), and dried under vacuum. An aliquot of the dry, selectively sulfonated polymer (2.34 g) was dissolved in a mixture of tetrahydrofuran (THF) and methanol (MeOH) (5/1 (v/v)) and the polymer bound sulfonic acid functionality was titrated to a thymol blue endpoint using a solution of sodium hydroxide (NaOH) (0.245 N) in methanol/water (80/20 (w/w)). This analysis found that 33.6 mol % of the polystyrene sites in the block copolymer had been sulfonated.

In Table 3, polymers labeled T-1, T-3, TS-1, TS-2, TS-3 and TS-4 were sulfonated using essentially the same technique. The quantities of reagents used in the subsequent experiments were slightly different which resulted in slightly different levels of sulfonation (mmol of sulfonate/g of polymer).

In a related experiment, a plastic triblock copolymer having sulfonation resistant end segments and a sulfonation susceptible interior segment was sulfonated with acetylsulfate. A triblock copolymer having poly-p-t-butylstyrene (ptBS) end segments and a polystyrene (S) interior segment, ptBS-S-ptBS (labeled polymer T-4.1, Table 2) (20 g), was dissolved in 1,2-dichloroethane (DCE) (500 g) and the solution heated to 49 C. The acetylsulfate reagent was prepared in a separate vessel by combining a cold (ice bath) solution of acetic anhydride (AcOAc) (18 g, 0.18 mol) in DCE (20-30 ml) with sulfuric acid (10.4 g, 0.11 mol). The cold solution of acetylsulfate was added with stirring to the polymer in DCE solution. Sulfonation conditions were maintained for 4.1 hr. The triblock copolymer, which had been selectively sulfonated in the interior segment, was isolated by coagulation in an excess of water, washed with water to remove acidic residues which were not bound to the polymer (until the wash water was neutral in pH), and dried under vacuum. An aliquot of the dry, selectively sulfonated polymer (1.04 g) was dissolved in a mixture of toluene and methanol (MeOH) (1/2 (v/v)) and the polymer bound sulfonic acid functionality was titrated to a thymol blue endpoint using a solution of sodium hydroxide (NaOH) (0.10 N) in methanol/water (80/20 (w/w)). This analysis found that 37 mol % of the polystyrene sites in the interior block of the copolymer had been sulfonated.

This procedure was repeated several times using somewhat different amounts of the sulfonating reagent affording the data reported in Table 3.

In a closely related experiment, a plastic triblock copolymer having poly-p-methylstyrene (pMS) end segments and a polystyrene (S) interior segment, pMS-S-pMS (labeled polymer P-1, Table 2) (20 g), was dissolved in 1,2-dichloroethane (DCE) (511 g) and the solution heated to 55 C. The acetylsulfate reagent was prepared in a separate vessel by combining a solution of acetic anhydride (AcOAc) (20 g, 0.20 mol) in DCE (10 g) with cold sulfuric acid (12.2 g, 0.12 mol). The cold solution of acetylsulfate was added with stirring to the polymer in DCE solution. Sulfonation conditions were maintained for 4 hr. The triblock copolymer, which had been selectively sulfonated in the interior segment, was isolated by coagulation in an excess of water, washed with water to remove acidic residues which were not bound to the polymer (until the wash water was neutral in pH), and dried under vacuum. An aliquot of the dry, selectively sulfonated polymer (1.0 g) was dissolved in a mixture of tetrahydrofuran and MeOH (2/1 (v/v)) and the polymer bound sulfonic acid functionality was titrated to a thymol blue endpoint using a solution of sodium hydroxide (NaOH) (0.135 N) in methanol/water (80/20 (w/w)). One would expect that about 35 mol % of the polystyrene sites in the interior block of the copolymer would have been sulfonated.

A plastic triblock copolymer having polyethylene-like (hydrogenated, low in vinyl content polybutadiene) end segments and a polystyrene (S) interior segment, PE-S-PE (labeled polymer E-1, Table 2) (20 g), was dispersed in 1,2-dichloroethane (DCE) (500 g) and the solution heated to 65 C. The acetyl sulfate reagent was prepared in a separate vessel by combining a solution of cold acetic anhydride (AcOAc) (20 g, 0.19 mol) in DCE (20 ml) with sulfuric acid (12.6 g, 0.13 mol). The cold solution of acetyl sulfate was added with stirring to the polymer in DCE slurry. Sulfonation conditions were maintained for 4 hr. The triblock copolymer, which had been selectively sulfonated in the interior segment, was isolated by decanting off the spent sulfonation reagent and the DCE, washed with water to remove acidic residues, which were not bound to the polymer (until the wash water was neutral in pH), and dried under vacuum. An aliquot of the dry, selectively sulfonated polymer was heated in the presence of xylene but did not dissolve. This was taken as supporting evidence that the polystyrene sites in the interior block of the copolymer had been sulfonated. In a like manner, the polymer could no longer be compression molded as a consequence of the strong interactions of the —SO3H sites present in the B block of the copolymer.

TABLE 3

Analysis of Sulfonated Polymers

| Polymer ID | Polymer Type | Sulfonation Level | |
|---|---|---|---|
| | | —SO$_3$H/polymer (mmol/g) | —SO$_3$H/Styrene (mol % basis styrene content of polymer) |
| COMPARATIVE EXAMPLES | | | |
| Aldrich-1 | S-E/B-S | 1.3 to 1.6 | 45 to 55 |
| G-1 | S-E/B-S | 0.9 | 30 |
| G-2 | S-E/B-S | 0.80 | 27 |
| A-1 | S-S/E/B-S | 0.6 | 17 |
| A-1.1 | S-S/E/B-S | 1.1 | 31 |
| A-2 | S-S/E/B-S | 1.6 | 25 |
| A-2 | S-S/E/B-S | 1.9 | 29 |
| A-3 | S-S/E/B-S | 2.3 | 38 |
| INVENTIVE EXAMPLES | | | |
| T-1 | (ptBS-S/E/B)$_n$ | 1.0 | 35 |
| T-2 | (ptBS-S/E/B)$_n$ | 1.3 | 34 |
| T-2.1 | (ptBS-S/E/B)$_n$ | 1.5 | 47 |
| T-2.1 | (ptBS-S/E/B)$_n$ | 1.0 | 32 |
| T-2.1 | (ptBS-S/E/B)$_n$ | 1.5 | 47 |
| T-2.1 | (ptBS-S/E/B)$_n$ | 1.4 | 46 |
| T-3 | (ptBS/S-S/E/B)$_n$ | 1.2 | 28 |
| T-4 | (ptBS-S)$_n$ | 0.7 | 9 |
| T-4.1 | (ptBS-S)$_n$ | 2.8 | 37 |
| T-4 | (ptBS-S)$_n$ | 2.0 | 27 |
| T-4 | (ptBS-S)$_n$ | 2.0 | 27 |
| T-4 | (ptBS-S)$_n$ | 2.3 | 31 |
| T-5 | (ptBS-S)$_n$ | 2.4 | 37 |
| T-5 | (ptBS-S)$_n$ | 1.8 | 27 |
| T-5 | (ptBS-S)$_n$ | 3.2 | 50 |
| T-5 | (ptBS-S)$_n$ | 1.5 | 23.8 |
| TS-1 | (ptBS-E/B-S)$_n$ | 1.5 | 47 |
| TS-1.1 | (ptBS-E/B-S)$_n$ | 1.8 | 58 |
| TS-2 | (ptBS-E/B-S)$_n$ | 2.5 | 64 |
| TS-2.1 | (ptBS-E/B-S)$_n$ | 1.8 | 46 |

TABLE 3-continued

Analysis of Sulfonated Polymers

| Polymer ID | Polymer Type | Sulfonation Level | |
|---|---|---|---|
| | | —SO$_3$H/polymer (mmol/g) | —SO$_3$H/Styrene (mol % basis styrene content of polymer) |
| P-1 | (pMS-S)$_n$ | 2.2 | 35 |
| E-1 | (PE-S)$_n$ | NA | NA |

Where S = styrene, E = ethylene, B = butylene, ptBS = para-tert-butylstyrene and E/B is hydrogenated polybutadiene, the starting polymers are described in Table 2. "Aldrich-1" was used as purchased from Aldrich Chemical Company (Product number 448885); functionality as defined in MSDS. "NA" means not analyzed.

Using the sulfonation technique described above, a wide range of polymers has been selectively sulfonated in the interior segment of the A-B-A block copolymers. Sulfonation levels have ranged from about 0.6 to about 2 8 mmol of sulfonate functionality per gram of polymer for polymers of the present invention (Polymers T-1, T-2, T-3, T-4, and P-1). The comparative example polymers which have been sulfonated in the end blocks (Aldrich-1 and G-1 which have styrene groups only in the A blocks) or indiscriminately sulfonated over all of the blocks of the copolymer (Polymers A-1 and A-2 which have reactive styrene groups in both the A and the B blocks), using the sulfonation technique described above, had functionality levels distributed over this same range. All of these polymers were carried forward in the synthesis of membranes.

Illustrative Embodiment #4

The sulfonated block copolymers were cast in air, at room temperature, from solvent (mixtures contained varying amounts of tetrahydrofuran (THF), methanol (MeOH), and toluene (MeBz), the ratios being adjusted to suit the solubility properties of the sulfonated block copolymers) onto the surface of Teflon coated foil. The resulting films were tested as cast (data labeled "Dry"). Test specimens were stamped from these membranes using a Mini-D die. Tensile testing was according to ASTM D412. The reported data represent averages of results of 3 to 5 tested samples depending on the variability of the sample results and amount of sample available.

In a representative experiment, an aliquot of an A-B-A triblock copolymer which had been selectively sulfonated in the elastomeric B block, Polymer T-2 in Table 3, was dissolved in a mixture of THF/MeOH and the solution was cast onto a Teflon coated foil surface. Several samples of the membrane were prepared for tensile testing (Mini-D die). The "dry" samples gave tensile at break values of 4410 psi (average) strength with an elongation of 290%. Clearly these were strong, elastic films. Several of the test samples stamped from the same film were equilibrated under water (for a day) prior to testing and the tensile testing apparatus was employed in such a way that the samples could be pulled while fully submerged under water (data labeled "Wet" in Table 4). On average, the wet samples had strength at break in tensile, under water, of 1790 psi with elongation at break of 280%. Even in the wet state, this membrane was strong and very elastic. Surprisingly, this triblock copolymer which had been selectively sulfonated in the interior segment had retained, when fully hydrated, over 40% of the strength of the analogous polymer when tested in the dry state; the wet polymer had essential the same elongation at break as had been observed when test in the dry state. An elastomeric membrane having excellent wet strength and elongation properties was prepared by solvent casting a polymer of the present invention.

As shown in Table 4, sulfonated adducts of Polymers T-1, T-3, T-2.1, and TS-1, illustrative embodiments of the present invention, afforded membranes with exceptional wet strength and elasticity.

In contrast to the surprising results obtained with the inventive polymers as described above, films cast from the comparative example polymers, polymers sulfonated selectively in the end blocks (Aldrich 1) and polymers non-selectively sulfonated in all segments (sulfonated adducts of Polymers A-1.1 and A-2), had poor wet tensile strengths. In the example employing the Aldrich 1 polymer, the wet test films were too weak to give a detectable response in the tensile test. With the exceptions of experiments with Polymers A-1 and G-1, the films from the comparative example polymers had lost nearly all (range from over 80 to 100% loss of tensile strength) of their strength when tested in the wet state by comparison to the properties measured on the samples tested when dry. Clearly films prepared from sulfonated block copolymers having these structures will be disadvantaged in applications where the membranes will get wet.

As will be shown later, the G-1 polymer and the A-1 polymer were not sufficiently sulfonated to have effective water transport properties. While these polymers demonstrated fair performance in the wet tensile test, they were not sulfonated to a sufficient level to give effective semi permeable membranes.

An aliquot of an A-B-A block copolymer having only plastic blocks (poly-p-t-butylstyrene end segments and a polystyrene interior segment), which had been selectively sulfonated in the polystyrene interior segment, T-4, was dissolved in THF and the solution was cast onto a Teflon coated foil surface. Several samples of the resulting membrane were prepared for tensile testing (Mini-D die). The "dry" samples gave a tensile strength at break value of 1800 psi (average) at an elongation of 14%. This was a very plastic material, which went through a yielding event with elongation and then failed. Several of the test samples stamped from the same film were equilibrated under water (for a day) prior to testing and the tensile testing apparatus was employed in such a way that the samples could be pulled while fully submerged under water (data labeled "Wet" in Table 4). On average, the wet samples had strength at break in tensile, under water, of 640 psi with elongation at break of 38%. In the wet state, this membrane was strong and more flexible. Surprisingly, this triblock copolymer which had been selectively sulfonated in the interior segment had retained, when fully hydrated, over 30% of the strength of the analogous polymer when tested in the dry state; the wet polymer had a substantially improved elongation at break by comparison to what had been observed when tested in the dry state. The flexibility of the polymer was enhanced as a consequence of the water selectively plasticizing the sulfonated polystyrene phase. A firm, plastic membrane having good wet strength and improved toughness when wet was prepared by solvent casting a polymer of the present invention. This polymer was prepared by selectively sulfonating a plastic triblock copolymer in the interior segment. Membranes derived from casting a related, sulfonated polymer, T-5, afforded even better results in the wet tensile test (see Experiments 91-57 and 91-74 in Table 4). As illustrated by membranes prepared from TS-2, insertion of a short rubber segment between the sulfonation resistant p-t-BS end segments and the sulfonation susceptible S interior segment afforded sulfonated materials with even better wet mechanical performance. The mechanical properties of these materials in the dry state were also quite good (see Polymers TS-2 and TS-2.1 in Table 4).

As shown in Table 4, the results for a membrane cast from a selectively sulfonated plastic triblock copolymer having poly-para-methylstyrene end segments and a polystyrene center segment were even more striking. In the dry state, this polymer was so brittle that a test sample could not be stamped from the "dry" as cast membrane; the specimen shattered in the stamping operation. The film was then soaked in water for a day. Test specimens were easily stamped from the wet film once the sulfonated polystyrene block had been plasticized by the water. Under water tensile testing found this polymer membrane to have good strength, 1800 psi tensile strength at break, and strikingly improved toughness.

For the results on the related, membranes prepared from the selectively sulfonated, plastic, A-B-A triblock copolymer having polyethylene end segments and a polystyrene interior block, see the data in Table 4.

It is apparent from these data that, when used in a wet environment, membranes prepared from thermoplastic block copolymers of the present invention, which are selectively sulfonated in the B block will have good strength, toughness, and flexibility properties. As it is envisioned that many of the applications for products of the present invention will be in wet environments, these materials will be substantially advantaged.

TABLE 4

Tensile Properties of Membranes Cast From Sulfonated Block Copolymers.

| Polymer ID | Polymer Type | Tensile Strength (psi) | | | Tensile Elongation (%) | | |
| --- | --- | --- | --- | --- | --- | --- | --- |
| | | Wet | Dry | W/D | Wet | Dry | W/D |
| COMPARATIVE EXAMPLES | | | | | | | |
| Aldrich-1 | S-E/B-S | 0 | 780 | 0 | 0 | 650 | 0 |
| G-1 | S-E/B-S | 650 | 1200 | 0.54 | 370 | 630 | 0.59 |
| A-1 | S-S/E/B-S | 770 | 3770 | 0.20 | 540 | 830 | 0.65 |
| A-1.1 | S-S/E/B-S | 460 | 3440 | 0.13 | 410 | 580 | 0.71 |
| A-2 | S-S/E/B-S | 230 | 2950 | 0.08 | 140 | 230 | 0.61 |
| A-2 | S-S/E/B-S | 90 | 3150 | 0.03 | 60 | 310 | 0.19 |
| A-3 | S-S/E/B-S | 1700 | 3360 | 0.51 | 300 | 230 | 1.3 |
| INVENTIVE EXAMPLES | | | | | | | |
| T-1 | (ptBS-S/E/B)$_n$ | 2366 | 3682 | 0.64 | 121 | 142 | 0.85 |
| T-2 | (ptBS-S/E/B)$_n$ | 1790 | 4410 | 0.41 | 280 | 290 | 0.97 |
| T-2.1 | (ptBS-S/E/B)$_n$ | 3300 | 3300 | 1.0 | 280 | 180 | 1.6 |

TABLE 4-continued

Tensile Properties of Membranes Cast From Sulfonated Block Copolymers.

| Polymer | | Tensile Strength (psi) | | | Tensile Elongation (%) | | |
|---|---|---|---|---|---|---|---|
| ID | Polymer Type | Wet | Dry | W/D | Wet | Dry | W/D |
| T-2.1 | (ptBS-S/E/B)$_n$ | 2430 | 3360 | 0.72 | 300 | 290 | 1.0 |
| T-2.1 | (ptBS-S/E/B)$_n$ | 2050 | 3850 | 0.53 | 140 | 220 | 0.66 |
| T-2.1 | (ptBS-S/E/B)$_n$ | 2270 | 4630 | 0.49 | 160 | 190 | 0.84 |
| T-3 | (ptBS/S-S/E/B)$_n$ | 2770 | 3660 | 0.76 | 310 | 260 | 1.19 |
| T-4 | (ptBS-S)$_n$ | 643 | 1799 | 0.36 | 38 | 14 | 2.71 |
| T-5 | (ptBS-S)$_n$ | 1480 | Brit | Inf | 66 | Brit | Inf |
| T-5 | (ptBS-S)$_n$ | 870 | Brit | Inf | 66 | Brit | Inf |
| T-5 | (ptBS-S)$_n$ | NA | | | | | |
| TS-1 | (ptBS-E/B-S)$_n$ | 2940 | 3194 | 0.92 | 510 | 390 | 1.3 |
| TS-1.1 | (ptBS-E/B-S)$_n$ | 1110 | 1440 | 0.77 | 180 | 28 | 6.4 |
| TS-2 | (ptBS-E/B-S)$_n$ | 1600 | 2130 | 0.75 | 150 | 7 | 21 |
| TS-2.1 | (ptBS-E/B-S)$_n$ | 4740 | 5870 | 0.81 | 5 | 16 | 3.2 |
| P-1 | (pMS-S)$_n$ | 1827 | Brit | Inf | 5 | Brit | Inf |
| E-1 | (PE-S)$_n$ | 111 | NA | NA | 6 | NA | NA |

Where S = styrene, E = ethylene, B = butylene, ptBS = para-tert-butylstyrene, E/B is hydrogenated polybutadiene, and PE = hydrogenated low vinyl content polybutadiene, "Aldrich-1" was used as purchased from Aldrich Chemical Company (Product number 44885), "Brittle" or "Brit" denotes a membrane that shattered when an attempt was made to stamp a tensile test specimen from the film, "Infinite" or "Inf" was reserved for the value of the ratio of wet to dry properties when the dry membrane was too brittle to test. NA = not analyzed Illustrative Embodiment #5

Figure 2:
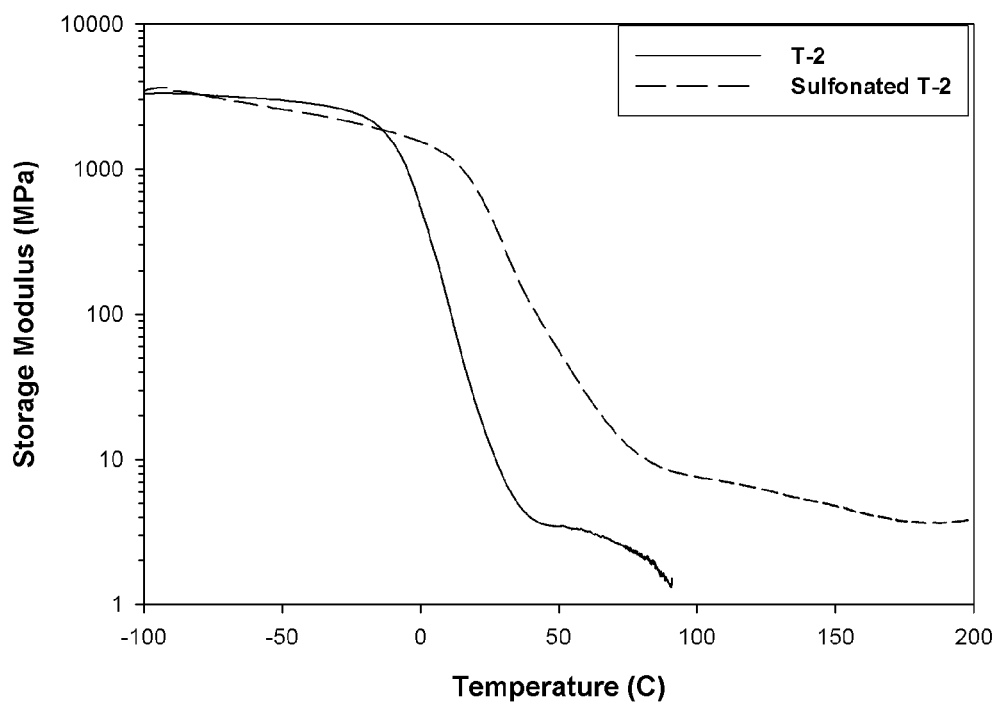
FIG. 2 shows a similar increase in the Tg of the interior block of sample T-2. These increases demonstrate that in both samples the interior block is sulfonated to a degree that results in a significant change in the physical properties of the sample.

In Illustrative Embodiment #5, the sulfonated polymers were tested by Dynamic Mechanical Analysis. Dynamic mechanical analysis was performed on both sulfonated and precursor polymers using a DMA 2900 manufactured by TA Instruments. Scans were performed using 10 Hz oscillation and a 2° C./min temperature ramp on solvent cast film samples. The temperature range tested was from −100 ° C. to 200 ° C. for the sulfonated polymers to −100 ° C. to 120 ° C. for the precursor polymers. FIG. 1 shows a comparison of the storage modulus of sample T-3 before and after sulfonation. This figure shows that the midpoint of the glass to rubber transition, Tg, of the S/EB interior block moves from approximately 15° C. to approximately 50° C. Similarly, FIG. 2 shows a similar increase in the Tg of the interior block of sample T-2. These increases demonstrate that in both samples the interior block is sulfonated to a degree that results in a significant change in the physical properties of the sample.

Illustrative Embodiment #6

Swelling studies on polymeric materials have been taken as a measure of dimensional stability (or lack thereof) for articles prepared from a particular polymer in the presence of a specific swelling agent. In the present case, swelling studies in water were carried out on the solution cast films of the sulfonated block copolymers described in Table 4. In the extreme, it would be desirable to have polymers sulfonated at very high levels (for good water transport performance) that afforded membranes with excellent dimensional stability (very little swelling) in the presence of water.

In an example of the present invention, a "dry" as cast film prepared from the selectively sulfonated adduct of an elastomeric A-B-A triblock copolymer having poly-p-t-butylstyrene end segments and an elastomeric interior block being a hydrogenated copolymer of butadiene and styrene was weighed (Polymer T-2), submerged in a pan of water for a day, removed from the water, blotted dry, and reweighed. From this experiment, it was discovered that the film had a 62% increase in weight as a result of being immersed in water for a day. Samples taken at shorter amounts of time demonstrated the film had reached an equilibrium weight gain in less than a few hours. The weight gain after 1 day under water was taken as a measure of the equilibrium swelling for this film. As shown in Table 5, the equilibrium swelling results are typically lower for films cast from the other selectively sulfonated in the interior segment copolymers, for both elastomeric and plastic precursor polymers. They would be expected to demonstrate even better dimensional stability when used in wet applications.

By comparison, the results of similar experiments conducted on films cast from the comparative example polymers which had been sulfonated either in the end blocks or indiscriminately in all parts of the block copolymer were inferior. In these systems, swelling could only be controlled by reducing the level of functionality of the polymer. At useful levels of sulfonation, swelling levels as high as 280% were observed; these films have very poor dimensional stability by comparison to polymers of the present invention. A lower level of swelling was realized in Comparative Example Experiments with Polymers A-1 and G-1 having lower levels of sulfonation. But, as will be shown later, the reduced level of swelling came at the cost of essentially no water transport performance. In the comparative example polymers, it was not possible to have a membrane that had both effective water transport properties and good dimensional stability (as measured by swelling experiments) in a wet environment. Block copolymers of the present invention which are selectively sulfonated in the center block were found to afford films that were advantaged in dimensional stability in wet environments.

TABLE 5

Water Uptake for Membranes Cast From Sulfonated Polymers.

| Polymer ID | Polymer Type | Sulfonation Level —SO$_3$H/polymer (mmol/g) | Equilibrium Swell (% wt gain) |
|---|---|---|---|
| COMPARATIVE EXAMPLES | | | |
| Aldrich 1 | S-E/B-S | 1.3–1.6 | 180 |
| G-1 | S-E/B-S | 0.9 | 11 |
| A-1 | S-S/E/B-S | 0.6 | 8 |

TABLE 5-continued

Water Uptake for Membranes Cast From Sulfonated Polymers.

| Polymer ID | Polymer Type | Sulfonation Level —SO$_3$H/polymer (mmol/g) | Equilibrium Swell (% wt gain) |
|---|---|---|---|
| A-1.1 | S-S/E/B-S | 1.1 | 110 |
| A-2 | S-S/E/B-S | 1.6 | 88 |
| A-2 | S-S/E/B-S | 1.9 | 280 |
| A-3 | S-S/E/B-S | 1.6 (avg) | 56 |
| INVENTIVE EXAMPLES | | | |
| T-1 | (ptBS-S/E/B)$_n$ | 1.0 | 30 |
| T-2 | (ptBS-S/E/B)$_n$ | 1.3 | 62 |
| T-2.1 | (ptBS-S/E/B)$_n$ | 1.5 | 27 |
| T-2.1 | (ptBS-S/E/B)$_n$ | 1.0 | 63 |
| T-2.1 | (ptBS-S/E/B)$_n$ | 1.5 | 9.0 |
| T-2.1 | (ptBS-S/E/B)$_n$ | 1.4 | 24 |
| T-3 | (ptBS/S-S/E/B)$_n$ | 1.2 | 35 |
| T-4 | (ptBS-S)$_n$ | 2.8 | 74 |
| T-5 | (ptBS-S)$_n$ | 1.8 | 41 |
| T-5 | (ptBS-S)$_n$ | 3.2 | 96 |
| T-5 | (ptBS-S)$_n$ | NA | 15 |
| TS-1 | (ptBS-E/B-S)$_n$ | 1.5 | 19 |
| TS-1.1 | (ptBS-E/B-S)$_n$ | 1.8 | NA |
| TS-2 | (ptBS-E/B-S)$_n$ | 2.5 | 15 |
| TS-2.1 | (ptBS-E/B-S)$_n$ | 1.8 | NA |
| P-1 | (Pms-S)$_n$ | 2.2 | 25 |
| E-1 | (PE-S)$_n$ | NA | 34 |

See footnote to Table 4 for an explanation of the symbols and abbreviations used in this table.

Illustrative Embodiment #7

The solvent cast films described in Illustrative Embodiment #4 and the related Comparative Example materials described in Table 4 were tested to determine the rate at which water passed from one side of the membrane to the other. The water vapor transmission (WVT) rate was measured on films about 1 mil thick using the ASTM E96-00 "desiccant" method. In this test a small, open topped vessel containing an activated, dry desiccant was covered with the membrane to be tested. The membrane was sealed to the top of the vessel and this assembly was weighed. The testing device was exposed to the atmosphere in a controlled temperature (75° F.(23.9° C.)) and controlled humidity (relative humidity 50%) for a week and reweighed to see how much water had passed through the membrane and been absorbed by the desiccant. Knowing the time of the test, the thickness and exposed surface area of the membrane, and the weight of the water absorbed, the WVT rate can be calculated and has been reported as Permeability (g of H2O/Pa.m.h.).

The membrane prepared from the inventive polymer, selectively sulfonated T-2, was found to have a water permeability of $1.2 \times 10^{-6}$ g/Pa.m.h., an effective transmission rate. In addition, this membrane had excellent wet strength and elongation properties. The polymer used in making this membrane was prepared by selectively sulfonating an elastomeric triblock copolymer in the interior segment. As shown in Table 6, membranes prepared from the other selectively sulfonated, elastomeric, A-B-A polymers of the present invention, Polymers T-1 and T-3, also had effective WVT rates and were superior to the comparative polymer membranes in wet strength and dimensional stability.

The membrane prepared from the inventive polymer, selectively sulfonated T-4, was found to have a water permeability of $9.0 \times 10^{-6}$ g/Pa.m.h., an effective transmission rate. This WVT rate exceeds (by a factor of about 3) that of any other polymer in Table 6. In addition, this membrane had good wet strength, demonstrated good toughness and flexibility, and had good dimensional stability in the presence of water. The polymer used in making this membrane was prepared by selectively sulfonating a thermoplastic triblock copolymer in the interior segment. As shown in Table 6, membranes prepared from the other selectively sulfonated, thermoplastic, A-B-A polymers of the present invention, Polymers P-1 and E-1, also had exceptional WVT rates and superior wet strength and dimensional stability in a wet environment. This property set offers a significant advance in the performance of membranes that are capable of transporting water.

As expected, several of the membranes prepared from sulfonated adducts of the comparative example polymers had effective water transmission rates with values ranging from $3.6 \times 10^{-7}$ to $2.6 \times 10^{-6}$ g/Pa.m.h. The membrane prepared from the sulfonated polymer A-1 sulfonated in Experiment 45-28 was the notable exception; there was essentially no flow of water through this membrane at all, permeability=$2.3 \times 10^{-9}$ g/Pa.m.h. The glaring problem with these membranes (Experiment 45-28)made from polymer A-1 was that they had little or no wet strength and had poor dimensional stability in the presence of water. They will be very difficult to use in applications that involve a wet environment. The membranes prepared according the current invention will have good water transport rates and will have robust mechanical properties in the presence of water.

TABLE 6

Water Vapor Transmission Rates for Membranes Solvent Cast From Sulfonated Triblock Copolymer Solutions.

| Polymer ID | Polymer Type | Equilibrium swelling (% wt gain) | Wet Tensile Strength (psi) | Permeability ($10^{-6}$ g/Pa·m·h) |
|---|---|---|---|---|
| COMPARATIVE EXAMPLES | | | | |
| Aldrich-1 | S-E/B-S | 180 | 0 | 3 |
| G-1 | S-E/B-S | 11 | 650 | 0.078 |
| A-1 | S-S/E/B-S | 8 | 770 | 0.0023 |
| A-1.1 | S-S/E/B-S | 110 | 460 | 1.5 |
| A-2 | S-S/E/B-S | 90 | 230 | 0.99 |
| A-2 | S-S/E/B-S | 280 | 90 | 2.6 |
| INVENTIVE EXAMPLES | | | | |
| T-1 | (ptBS-S/E/B)$_n$ | 30 | 2370 | 1.7 |
| T-2 | (ptBS-S/E/B)$_n$ | 62 | 1790 | 1.2 |
| T-3 | (ptBS/S-S/E/B)$_n$ | 35 | 2770 | 0.30 |
| T-4 | (ptBS-S)$_n$ | 74 | 640 | 9.0 |
| P-1 | (pMS-S)$_n$ | 25 | 1830 | NA |
| E-1 | (PE-S)$_n$ | 34 | 11 | NA |

See footnote to Table 4 for an explanation of the symbols and abbreviations used in this table.

Illustrative Embodiment #8 Preparation of a Selectively Sulfonated (A-B-D)x Block Copolymer (Hypothetical)

A living triblock copolymer arm, ptBS-S-Bd-Li, would be prepared using living anionic polymerization methods with sequential addition of the monomers. The living triblock copolymer arm would be coupled affording a mixture of linear and branched polymer chains having sulfonation resistant end segments of poly-para-tert-butylstyrene (ptBS), sulfonation susceptible inner segments of polystyrene (S) and the precursor for an impact modifying, sulfonation resistant block of hydrogenated polybutadiene (E/B) in the center of the molecule.

In a representative experiment, the polymerization of 26 g of para-tert-butylstyrene monomer in a mixture containing 940 g of cyclohexane and 60 g of dry diethyl ether would be initiated, under anionic polymerization conditions, at 40 C, by the addition of 1 mmol of sec-BuLi. Upon complete conversion of the monomer, an analytical sample of the living poly-para-tert-butylstyrene would be terminated by the addition of an excess of MeOH and the terminated product analyzed by a GPC method to find a polymer having a true MW=26,000 g/mol. Having made the first block of the polymer arm, 52 g of styrene monomer would be added to the living polymer solution. Upon complete conversion of the monomer, an analytical sample of the living poly-para-t-butylstyrene-polystyrene diblock copolymer would be terminated by the addition of an excess of MeOH and the terminated product analyzed by a GPC method to find a polymer having a true MW=78,000 g/mol. This would correspond to a ptBS-S diblock copolymer having segment molecular weights of 26,000-52,000 respectively. Having made the second block of the copolymer arm, 20 g of 1,3-butadiene monomer would be added to the living polymer solution. Upon complete conversion of the monomer, an analytical sample of the living poly-para-t-butylstyrene-polystyrene-polybutadiene triblock copolymer would be terminated by the addition of an excess of MeOH and the terminated product analyzed by a GPC method to find a polymer having a true MW=98,000 g/mol. This would correspond to a ptBS-S-Bd block copolymer having segment molecular weights of 26,000-56,000-20,000 respectively. Analysis of the triblock copolymer using H-NMR would be expected to find about 40% of the butadiene to have added by a 1,2-addition mechanism. Having made the third block of the copolymer arm, the living polymer arms would be coupled by the addition of 0.04 mmol of tetramethoxysilane (TMOS) (Si/Li=0.4/1(mol/mol)). Analysis of the coupled polymer solution using a GPC method would be expected to find a mixture of branched (major component) and linear coupled polymers, (ptBS-S-Bd)TMOS with less than 10% of the arms remaining as unlinked triblock copolymer chains.

The cyclohexane/diethyl ether solution of the freshly polymerized (ptBS-S-Bd)TMOS mixture would be transferred to a pressure vessel. Hydrogen would be added to a pressure of 700 psig. A suspension (in an amount equivalent of 0.2 g of Co) containing the reaction product derived from the addition of Co(neodecanoate)2 and triethylaluminum (Al/Co=2.6/1 (mol/mol) would be added to the reactor to initiate hydrogenation. When the hydrogenation reaction is complete (99% of the C=C centers were hydrogenated as measured using a H-NMR technique), excess hydrogen gas would be vented off and the selectively hydrogenated polymer, (ptBS-S-E/B) TMOS, would be contacted with an excess of 10% wt sulfuric acid in water and exposed to the air (Care would be taken in this step to avoid the formation of an explosive mixture of hydrocarbon and air.). Contacting the polymer cement with air in the presence of an excess of acid will result in the oxidation of the hydrogenation catalyst and extraction of the inorganic catalyst residues into the aqueous phase. The polymer solution would be washed with water to remove any acid species that might be in the organic phase. About 100 g of the selectively hydrogenated polymer would be recovered by coagulation with MeOH, collection by filtration, and dried. An aliquot of this polymer would be analyzed by DSC and the Tg of the impact modifier phase would be found to be below 0° C.

An aliquot of the new polymer, (ptBS-S-E/B)TMOS would be selectively sulfonated in the center segment using the procedure outlined in Experiment 43-5 used for T-4. A 20 g portion of the new polymer having a sulfonation resistant, impact modifying, center block would be dissolved in 1,2-dichloroethane (DCE) (500 g) and the solution heated to 49 C. The acetyl sulfate reagent would be prepared in a separate vessel by combining a cold (ice bath) solution of acetic anhydride (AcOAc) (18 g, 0.18 mol) in DCE (20-30 ml) with cold sulfuric acid (10.4 g, 0.11 mol). The cold solution of acetyl-sulfate would be added with stirring to the polymer in DCE solution. Sulfonation conditions would be maintained for 4.1 hr. The multiblock copolymer, which would have been selectively sulfonated in the inner styrene segments, would be isolated by coagulation in an excess of water, washed with water to remove acidic residues which were not bound to the polymer (until the wash water was neutral in pH), and dried under vacuum. An aliquot of the dry, selectively sulfonated polymer (1.04 g) would be dissolved in a mixture of toluene and methanol (MeOH) (½ (v/v)) and the polymer bound sulfonic acid functionality would be titrated to a thymol blue endpoint using a solution of sodium hydroxide (NaOH) (0.14 N) in methanol/water (80/20 (w/w)). This analysis would be expected to find that about 37 mol % of the polystyrene sites in the interior block of the copolymer had been sulfonated.

An aliquot of the selectively sulfonated A-B-D-B-A block copolymer having sulfonation resistant end blocks (poly-p-t-butylstyrene end segments) and impact modifying center block (hydrogenated polybutadiene) and having sulfonation susceptible polystyrene inner segments would be dissolved in a THF/MeOH (3/1(v/v)) solvent mixture and the solution would be cast onto a Teflon coated foil surface. Several samples of the resulting membrane would be prepared for tensile testing (Mini-D die). The "dry" samples would be expected to give tensile strength at break values in excess of 1800 psi (average) at an elongation of more than 14%. This would be a very flexible material. Several of the test samples stamped from the same film would be equilibrated under water (for a day) prior to testing and the tensile testing apparatus would be employed in such a way that the samples could be pulled while fully submerged under water. On average, the wet samples would be expected to have strength at break in tensile, under water, in excess of 500 psi with elongation at break in excess of 38%. In the wet state, this membrane would be strong and flexible. Surprisingly, this triblock copolymer which had been selectively sulfonated in the inner styrene segments would be expected to have retained, when fully hydrated, over 30% of the strength of the analogous polymer when tested in the dry state. The flexibility of the polymer would have been enhanced as a consequence of the water selectively plasticizing the sulfonated polystyrene phase. A firm, flexible, membrane having good wet strength and improved toughness when wet would have been prepared by solvent casting a polymer of the present invention. This polymer would have been prepared by selectively sulfonating a polymer having an impact modifying block in the center (interior) of the molecule.

Swelling studies on the new, selectively sulfonated polymer, conducted according the process outlined in Illustrative Embodiment #6, would be expected to find the selectively sulfonated (ptBS-S-E/B)TMOS polymer to take up less than 100% of its weight in water at equilibrium. From this result, it would be concluded that materials prepared from this polymer would have good dimensional stability in the presence of water.

Using the procedure outlined in Illustrative Embodiment #7, membranes prepared from the selectively sulfonated (ptBS-S-E/B)TMOS polymer would have been tested for water transport rates. This test would be expected to find these polymers to have water permeability values in excess of 0.1×

10–6 g/Pa.m.h. From this result, it would be concluded that these membranes are very effective for the transport of water.

These experiments would be expected to show that the selectively sulfonated polymer having sulfonation resistant outer blocks, sulfonation susceptible inner segments, and a sulfonation resistant, impact modifying block in the center of the molecule would afford articles having good dimensional stability in the presence of water, useful levels of strength, excellent toughness and flexibility, and effective water transport properties.

Illustrative Embodiment #9. Control of Mechanical Performance and State of Water via Casting Conditions In this example an aliquot of the sulfonated block copolymer TS-1 based on (A-D-B)nX which had been selectively sulfonated in the B block was cast from three different solvent mixtures (Table 7), in air, at room temperature, onto the surface of Teflon coated foil. The resulting films were tested as cast (data labeled "Dry"). Test specimens were tested for water uptake, water permeation, state of water in the film, and tensile strength in both the wet and dry state. Water swelling studies were performed as described in Illustrative Embodiment #6, and wet and dry tensile measurements were performed as described in Illustrative Embodiment #4. Atomic force microscopy was performed to view the morphology of the three membranes. The state of water was measured using the differential scanning calorimetry (DSC) method set forth in the publications by Hickner and coworkers titled "State of Water in Disulfonated Poly(arylene ether sulfone) Copolymers and a Perfluorosulfonic Acid Copolymer (Nafion) and Its Effect on Physical and Electrochemical Properties", Macromolecules 2003, Volume 36, Number 17, 6281-6285 and "Transport in sulfonated poly(phenylene)s: Proton conductivity, permeability, and the state of water", Polymer, Volume 47, Issue 11, Pages 4238-4244. Water permeation rate measurements were measured by the method set forth in the publication by N. S. Schneider and D. Rivin "Solvent transport in hydrocarbon and perfluorocarbon Ionomers", Polymer, Volume 47, Issue 9, Pages 3119-3131.

TABLE 7

Effect of casting conditions on Membrane properties.

| Solvent mixture | Dry Tensile (PSI) | Wet Tensile (PSI) | Water Uptake (wt %) | Water Perm rate g-mil/day-m² | Water heat of fusion ($\Delta H_f$) (J/g) |
|---|---|---|---|---|---|
| 90/10 Toluene/MeOH | 3100 | 2600 | 18 | 2700 | 191 |
| 80/20 THF/Toluene | 3800 | 2700 | 21 | 3500 | 257 |
| 50/50 THF/Toluene | 4300 | 2300 | 21 | 1160 | 65 |

Atomic force microscopy (FIG. 3) shows that different structures were formed from the three different casting solutions. While all three films have exceptional wet and dry strength, the strength of each film differed (Table 7). Each film also had similar water uptake of 18 to 21 wt % (Table 7).

It is surprising that each film has a different mechanism of storing water as measured by DSC (FIG. 4). FIG. 4 shows two overlapping endothermic peaks for each sample, which consist of the broad melting peak range from –30° C. to 10° C., assigned to the weakly bound water and the sharp melting peak at 0° C. due to the free water. The amount of bound and free water is indicated by the location and broadness of the melting peaks and variations in $\Delta Hf$ (Table 7). Low values of $\Delta Hf$ indicate tightly bound water ($\Delta Hf$ for bulk water is 334 J/g), as the tightly bound water is not able to freeze. Varying the relative amounts of bound versus free water allows for the tuning of transport properties with a single sulfonated polymer. In this example the water permeation rate is increased by more than a factor of three via changes in the amount of bound water.

Illustrative Embodiment #10

In Illustrative Embodiment #10, the sulfonated polymers were tested for mechanical stability in boiling water. A piece of sulfonated polymer membrane approximately 0.75" wide by 3" long was suspended in a container of boiling water. The lower end of the film was weighed down with a 3 g binder clip to prevent the sulfonated membrane from floating in the water. After boiling the membrane for 15 minutes, the samples were removed and measured for changes in dimension. The results are shown in Table 8. Both the 0091-49 and 0091-67A-3 and G-2 samples (comparative examples) gave undesirable results. The samples swelled to such a large extent that they began to tear at the clips during the testing and tore upon removal from the clips after testing. Surprisingly, the 0091-85 and 0091-91TS-1 and TS-2 samples (samples of the present invention) did not swell noticeably and retained their original dimensions following the testing. This is feature is highly desirable in applications such as methanol fuel cells as a clamped membrane would potentially be cycled through wet and dry atmospheres and dimensional stability is paramount.

TABLE 8

Swelling and membrane stability in boiling water.

| Polymer type | Polymer ID | Swelling (% increase in size) | Observation |
|---|---|---|---|
| S-S/E/B-S | A-3 | 180 | Sample broke upon extraction from water |
| S-E/B-S | G-2 | 175 | Sample tearing at clips due to swelling and tore upon removal from clamps |
| (ptBS-E/B-S)n | TS-1 | <10 | Slight shrinkage after drying |
| (ptBS-E/B-S)n | TS-2 | <10 | Slight embrittlement after drying |

What is claimed is:

1. A process for preparing sulfonated block copolymers that are solid in water having at least two polymer end blocks A and at least one polymer interior block B, the process comprising sulfonating said interior block B until said block B is substantially sulfonated, and wherein:
   a. each A block is a polymer block resistant to sulfonation and each B block is a polymer block susceptible to sulfonation, said A and B blocks containing no significant levels of olefinic unsaturation;
   b. each A block independently having a number average molecular weight between 1,000 and 60,000 and each B block independently having a number average molecular weight between 10,000 and 300,000;
   c. each A block comprising at least one segment of one or more polymerized para-substituted styrene monomers and optionally one or more segments selected from polymerized (i) ethylene, (ii) alpha olefins of 3 to 18 carbon atoms; (iii) 1,3-cyclodiene monomers, (iv) monomers of conjugated dienes having a vinyl content less than 35 mol percent prior to hydrogenation, (v)

acrylic esters, (vi) methacrylic esters, and (vii) mixtures thereof, wherein any segments containing polymerized 1,3-cyclodiene or conjugated dienes are subsequently hydrogenated;

d. each B block comprising segments of one or more vinyl aromatic monomers selected from polymerized (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof;

e. said B blocks are sulfonated to the extent of 10 to 100 mol percent, based on the units of vinyl aromatic monomer in said B blocks; and f. the mol percent of vinyl aromatic monomers which are unsubstituted styrene monomers, ortho-substituted styrene monomers, meta-substituted styrene monomers, alpha-methylstyrene, 1,1-diphenylethylene and 1,2-diphenylethylene in each B block being between 10 mol percent and 100 mol percent; and g. said sulfonated block copolymer is non-dispersible and solid in water, and has a tensile strength greater than 100 psi in the presence of water according to ASTM D412 after immersion in water for 24 hours.

2. The process according to claim 1, wherein said end blocks A have essentially no sulfonated monomers.

3. The process according to claim 1, wherein the B block is sulfonated with acyl sulfate as a sulfonation reagent.

4. The process according to claim 2, wherein the acyl sulfate is acetyl sulfate.

5. The process according to claim 1, wherein the B block is sulfonated with sulfur trioxide as a sulfonation reagent.

6. The process according to claim 5, wherein the sulfur trioxide is modified with an ether.

7. The process according to claim 1, wherein said B blocks are sulfonated to the extent of 10 to 100 mol percent, based on the units of vinyl aromatic monomer in said B blocks.

8. The process according to claim 1, wherein substantially sulfonated means that at least about 90 percent of the total sulfonation of the block copolymer occurs in the mid block B.

9. The process according to claim 1, each A block is a segment of one or more polymerized para-substituted styrene monomers.

10. The process according to claim 1, wherein said A block comprises up to 15 mol percent of polymerized monomers selected from (i) unsubstituted styrene monomers, (ii) ortho-substituted styrene monomers, (iii) meta-substituted styrene monomers, (iv) alpha-methylstyrene, (v) 1,1-diphenylethylene, (vi) 1,2-diphenylethylene and (vii) mixtures thereof.

11. The process according to claim 1, wherein the block copolymer further comprises at least one polymer block D having a glass transition temperature of less than 20° C. and a number average molecular weight of between 1,000 and 50,000.

12. The process according to claim 1, wherein the sulfonated block copolymer has a water permeability greater than $0.1$ times $10^{-6}$ grams per Pascal.meter.hour, according to ASTM E96-00 "desiccant" method, a wet tensile strength greater than 500 psi according to ASTM D412, and a swellability of less than 100% weight after immersion in water for 24 hours.

13. The process according to claim 1, further comprising forming the sulfonated block copolymer into an article having a ratio of wet tensile strength to dry tensile strength greater than 0.3.

14. The process according to claim 1, wherein the interior block B is a hydrogenated copolymer of one or more unsubstituted styrene monomers, and monomers of conjugated dienes having a vinyl content of 20 to 80 mol percent prior to hydrogenation.

15. The process according to claim 1, wherein said B block is a random copolymer, a tapered copolymer or a controlled distribution copolymer.

16. The process according to claim 1, wherein the block copolymer has the general configuration A-D-B-D-A, A-B-D-B-A, (A-D-B)nX, (A-B-D)nX, A-B-A, A-B-A-B-A, (A-B-A)nX, or (A-B)nX, or mixtures thereof, where n is an integer from 2 to about 30, and X is coupling agent residue.

17. The process according to claim 16, wherein said D block is selected from the group consisting of (i) a polymerized or copolymerized conjugated diene selected from isoprene, 1,3-butadiene having a vinyl content prior to hydrogenation of between 20 and 80 mol percent, (ii) a polymerized acrylate monomer, (iii) a silicon polymer, (iv) polymerized isobutylene and (v) mixtures thereof, wherein any segments containing polymerized 1,3-butadiene or isoprene are subsequently hydrogenated.

18. An article formed at least in part from a composition prepared by the process according to claim 1, said article being selected from the group consisting of fuel cells, fabrics, coated fabrics, membranes, filtration membranes, desalination membranes, air conditioning membranes, heat recovery membranes, coatings for membranes, personal hygiene articles, adhesives, hydrogels, antifouling coatings, water absorption articles, electrode assemblies, and marine coatings.

* * * * *